United States Patent
Betke et al.

(10) Patent No.: US 11,795,134 B2
(45) Date of Patent: *Oct. 24, 2023

(54) ESTER COMPOUNDS, METHOD FOR THE PRODUCTION THEREOF AND USE THEREOF

(71) Applicants: Klüber Lubrication München SE & Co. KG, Munich (DE); Universität Bielefeld, Bielefeld (DE)

(72) Inventors: Tobias Betke, Bielefeld (DE); Carmen Plass, Bielefeld (DE); Harald Gröger, Bielefeld (DE); Dirk Loderer, Munich (DE); Stefan Seemeyer, Munich (DE); Thomas Kilthau, Munich (DE); Ling Ma, Munich (DE)

(73) Assignees: Klüber Lubrication München SE & Co. KG, Munich (DE); Universität Bielefeld, Bielefeld (DE)

( * ) Notice: Subject to any disclaimer, the term of this patent is extended or adjusted under 35 U.S.C. 154(b) by 196 days.

This patent is subject to a terminal disclaimer.

(21) Appl. No.: 16/949,433

(22) Filed: Oct. 29, 2020

(65) Prior Publication Data

US 2021/0061750 A1  Mar. 4, 2021

Related U.S. Application Data

(62) Division of application No. 16/493,830, filed as application No. PCT/EP2018/000197 on Apr. 11, 2018, now Pat. No. 10,829,436.

(30) Foreign Application Priority Data

Apr. 13, 2017 (DE) .................. 10 2017 003 647.0
Apr. 10, 2018 (DE) .................. 10 2018 002 891.8

(51) Int. Cl.
| | | |
|---|---|---|
| *C07C 69/67* | (2006.01) | |
| *C07C 67/02* | (2006.01) | |
| *C10M 105/42* | (2006.01) | |
| *C12P 7/62* | (2022.01) | |
| *C10N 70/00* | (2006.01) | |

(52) U.S. Cl.
CPC .............. *C07C 69/67* (2013.01); *C07C 67/02* (2013.01); *C10M 105/42* (2013.01); *C12P 7/62* (2013.01); *C10M 2207/301* (2013.01); *C10N 2070/00* (2013.01)

(58) Field of Classification Search
CPC ...... C07C 69/02; C07C 69/67; C10M 105/42; C12P 7/62
See application file for complete search history.

(56) References Cited

U.S. PATENT DOCUMENTS

| | | | | |
|---|---|---|---|---|
| 10,829,436 | B2 * | 11/2020 | Betke ................. | C07C 67/02 |
| 2006/0276609 | A1 ‡ | 12/2006 | Lysenko ............ | C08G 18/4288 528/44 |
| 2010/0249357 | A1 ‡ | 9/2010 | Popa .................. | C08G 18/718 528/26 |
| 2014/0252281 | A1 * | 9/2014 | Han .................... | H01B 3/24 554/167 |

FOREIGN PATENT DOCUMENTS

EP          1 051 465 A1 ‡ 11/2000 .......... C10M 101/04

OTHER PUBLICATIONS

Bodalo, A., et al., "Production of Ricinoleic Acid Estolide with Free and Immobilized Lipase from Candida Rugosa,"Biochemical Engineering Journal 39 (2008) 450-456 (7 pages).‡
International search report corresponding to international application No. PCT/EP2018/000197 dated Jun. 27, 2018 (12 pages).‡
Metzger, Jürgen O. & Biermann, Ursula, "Alkylaluminum Chloride Catalyzed Ene Reactions of Formaldehyde with Unsaturated Carboxylic Acids, Esters and Alchohols," Synthesis, May 1, 1992, Section 463-465 (3 pages).‡

* cited by examiner
‡ imported from a related application

*Primary Examiner* — Yong L Chu
(74) *Attorney, Agent, or Firm* — Maginot, Moore & Beck LLP

(57) ABSTRACT

The invention relates to ester compounds of the general formula (I)

(I)

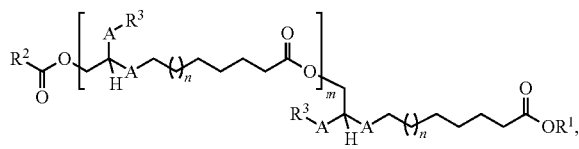

to a process for preparation thereof and to the use thereof. These ester compounds may contain a mixture of at least two compounds of the general formula (I).

10 Claims, 6 Drawing Sheets

Lit-1

General structure of the estolide compounds known from the literature (Ia)

Particularly preferred representatives of the inventive compounds using the example of the oleic acid derivatives (Ia)

Particularly preferred representatives of the inventive compound using the example of the oleic acid derivatives (Ib)

Particularly preferred representatives of the inventive compounds using the example of the oleic acid derivatives (Ic)

Preferred synthesis strategies proceeding from oleic acid and incorporating a hydroformylation for preparation of compounds 5

Preferred synthesis strategies proceeding from oleic acid and with incorporation of an ene reaction for preparation of compounds 5

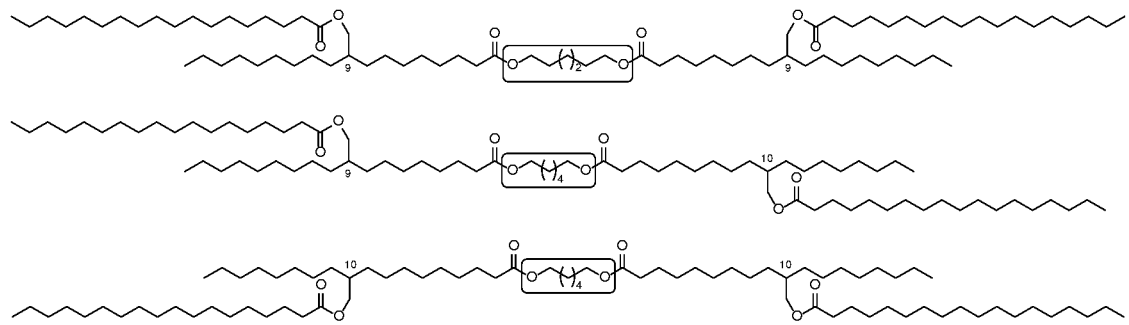

Figure 7

Particularly preferred representatives of the inventive compounds of the preferred general structure (Ib), prepared proceeding from 1,6-hexanediol as diol component

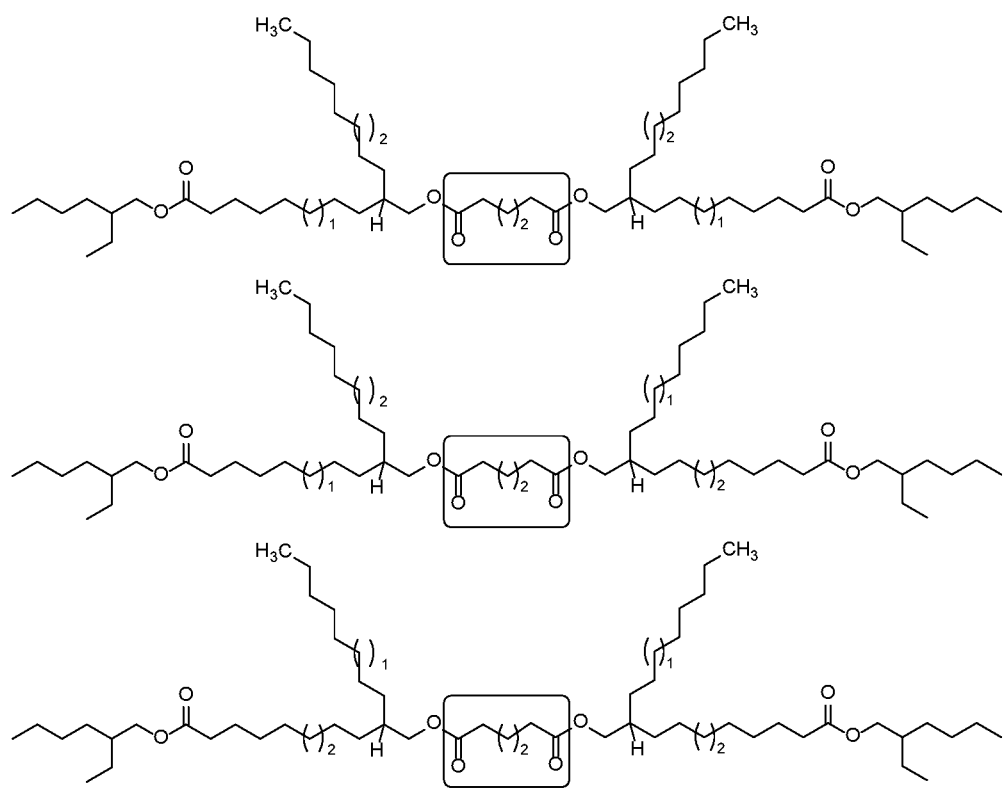

Figure 8

Particularly preferred representatives of the inventive compounds of the preferred general structure (Ic), prepared proceeding from n-hexanedicarboxylic acid as dicarboxylic acid component Particularly preferred representatives of the inventive compounds of the preferred general structure (Ic), prepared proceeding from the dicarboxylic acid Pripol 1013 as dicarboxylic acid component

ESTER COMPOUNDS, METHOD FOR THE PRODUCTION THEREOF AND USE THEREOF

PRIORITY CLAIM

This application is a divisional of co-pending U.S. application Ser. No. 16/493,830, which issued as U.S. Pat. No. 10,829,436, on Nov. 10, 2020, and which is a 35 U.S.C. 371 National Stage application of PCT/EP2018/000197, filed Apr. 11, 2018 and claiming priority to German Application Nos. DE 10 2017 003 647.0, filed on Apr. 13, 2017, DE 10 2018 002 891.8, filed on Apr. 10, 2018. The entire contents of the above-mentioned patent applications are incorporated herein by reference as part of the disclosure of this U.S. application.

BACKGROUND

The invention relates to novel ester compounds of the general formula (I)

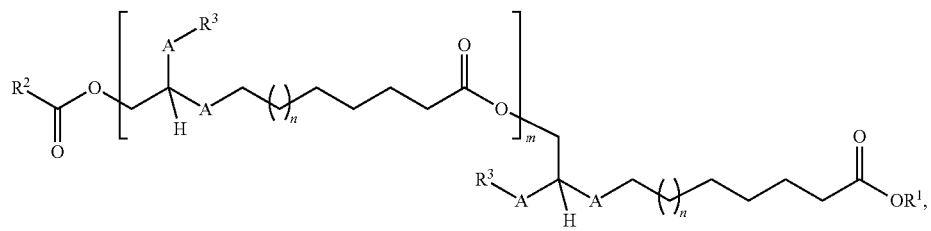

(I)

to a process for preparation thereof and to the use thereof. These ester compounds may contain a mixture of at least two compounds of the general formula (I).

Ester compounds have been used ever more frequently in lubricant formulations in the last few years. Since the ester units in the ester compounds in natural oils and also in synthetic ester oils are prone to hydrolysis, there is a great need for ester compounds that meet the high demands for use in lubricants. In the case of the known ester compounds, when the lubricant is used in the presence of water, the ester is hydrolyzed to the fatty acid and the alcohol. This reaction can be catalyzed, for example, by acids or bases or by copper. This results in the destruction of the molecules, as a result of which the lubricants lose their lubricating effect.

Furthermore, conventional lubricants, for example based on native esters, are unsuitable for high-temperature applications since they can be destroyed at high temperatures by oxidation and/or thermal decomposition processes and by polymerization, and hence their lubricating properties and effects are greatly restricted. In decomposition reactions, the lubricant is cleaved to give volatile components of low molecular weight. The evaporating of these volatile components leads to unwanted changes in viscosity and loss of oil, and to excess vapor formation. This likewise results in a loss of lubricity. The polymerization also causes the lubricants to lose their lubricity owing to the formation of insoluble polymerization products. This soiling has to be removed, which increases maintenance operations. Furthermore, chemical wastes are produced, which have to be disposed of in a complex manner. Owing to the increased cleaning and maintenance work, there is an increase in the shutdown times of the devices to be lubricated. Overall, the use of unsuitable lubricants in high-temperature applications leads to higher costs since the machinery is soiled and there is a high demand for lubricants. Furthermore, there is a drop in product quality.

In order to meet the various demands, lubricants must have, among other qualities, high stability, low coefficients of friction and high wear resistances. High temperatures often occur in the case of use in chains, ball bearings and slide bearings, in motor vehicle technology, in conveying technology, in mechanical engineering, in office technology and industrial plants and machinery, but also in the fields of domestic appliances and consumer electronics. High processing temperatures often occur, for example, in food processing, as in the case of cooking, baking, boiling, roasting, braising, sterilizing, frying and steaming. Various equipment is used in these operations. Lubrication of this equipment requires high-temperature-resistant lubricants.

Particular demands are made on the base oils for lubrication of equipment for the processing of foods in relation to environmental compatibility and toxicity. In principle, a food-compatible lubricant H1 should be suitable when the lubricant can come into indirect or direct contact with foods, semi-luxury goods and foodstuffs. The preferred fields of use in the food industry include chains in baking ovens and other high-temperature applications, and also transport gears, especially trolleys and bearings thereof.

These lubricants are subject to legal requirements, such as certification under NSF/H1 or NSF/H2.

In the case of applications of lubricants in the marine sector that are usually below the waterline, there is the risk of contamination of the marine or water environment as a result of escape of lubricants. Even though attempts are made to seal the water side as best possible in these applications, lubricant losses are an everyday occurrence.

According to a source at the United States Environmental Protection Agency in 2011, different ship constructions lose from less than one liter of lubricant up to 20 liters per day per ship. Good biodegradability of the lubricant here is a prerequisite for high environmental compatibility of the lubricants. Generally, such applications are regulated by legal requirements or standards, for example VGP, Eco-Label or OSPAR.

However, the lubricants known to date are unable to meet all these requirements.

There have already been proposals to use what are called estolide compounds in lubricants. These ester compounds, which are generally based on vegetable oils, are synthesized according to S. C. Cermak et al., *Industrial Crops and Products* 2013, 46, 386-392. According to this literature and patent specification EP 1 051 465 B1, this affords compounds of the general structure Lit-1 shown in FIG. 1, where x and y are equal to or greater than 1, x+y is 10, n is equal to or greater than 1, R is $CHR_1R_2$, $R_1$ and $R_2$ are each independently selected from hydrogen and saturated or unsaturated, branched or unbranched, substituted or unsubstituted and C1 to C36 hydrocarbons, $R_3$ is a structural fragment resulting from oleic acid, stearic acid or other fatty acids, and the preferred position of the secondary ester branch is at the 9 or 10 position (corresponding to x=5 or 6 and y=5 or 4).

These estolide compounds of the Lit-1 type are prepared according to the above-cited literature by addition of a fatty acid onto the C=C double bond of the next fatty acid, so as to obtain corresponding dimers (n=0) and additionally also tri-, tetra-, penta- and hexamers (n=1, 2, 3, 4). However, the structure shown, from the perspective of scientific representation of a repeat unit, cannot be correct since the linkage of the repeat unit is not apparent therefrom. Disadvantages of this process are the low selectivity (which leads correspondingly not to a defined product compound but to a mixture of dimer and oligomer mixtures), the harsh reaction conditions, the low yield and the complex separation of dimer/oligomer mixtures. The two concluding steps are then the hydrogenation of the remaining C=C double bond and the esterification of the remaining carboxylic acid group, where the alcohol component used is preferably 2-ethylhexan-1-ol.

SUMMARY OF THE DISCLOSURE

It is therefore an object of the present invention to provide novel ester compounds which meet the abovementioned demands for use in lubricants and which is producible from simple and readily available, preferably renewable, raw materials as starting materials by a sustainable and environmentally friendly route. Furthermore, the synthesis method is to have a high selectivity, a high yield is to be achieved and simple workup is to be possible.

This object is achieved by the provision of novel ester compounds and suitable synthesis methods for preparation thereof.

The ester compounds of the invention have the general formula (I) shown below and are a mixture of at least two compounds of the general formula (I)

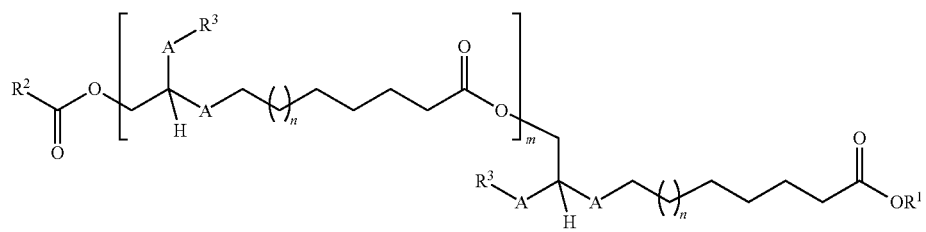

in which
the A radical is selected from the group consisting of $CH_2$, $CH_2CH_2$, cis-CH=CH and/or trans-CH=CH,
n is 0 or 1 to 20,
m is 0 or 1 to 20,
the $R^1$ radical is selected from the group consisting of hydrogen, branched or unbranched $C_1$- to $C_{60}$-alkyl radicals, branched or unbranched $C_2$- to $C_{60}$-alkenyl radicals, $C_7$- to $C_{60}$-arylalkyl radicals, $C_1$- to $C_{60}$-heteroarylalkyl radicals, $C_6$- to $C_{60}$-aryl radicals, and/or cyclically saturated or unsaturated $C_5$- to $C_{60}$-alkyl radicals, where these are unsubstituted or mono- or polysubstituted by at least one substituent selected from the group of OH, $R^4$, $R^5$, O-acetyl, the $R^2$ radical is selected from the group consisting of H, branched or unbranched $C_2$- to $C_{60}$-alkyl radicals, $C_2$- to $C_{60}$-heteroalkyl radicals, $C_7$- to $C_{60}$-arylalkyl radicals, $C_6$- to $C_{60}$-heteroarylalkyl radicals, $C_6$- to $C_{60}$-aryl radicals, and/or cyclically saturated or unsaturated $C_5$- to $C_{60}$-alkyl radicals, where these are unsubstituted or mono- or polysubstituted by at least one substituent selected from the group of OH, O—C(O)—$R^1$, $CH_2OH$, $CO_2H$, $CO_2R^1$, $R^5$, and additionally, in the case that m=1 to 20, also branched or unbranched $C_2$- to $C_{60}$-alkenyl radicals or methyl, where this is unsubstituted or mono- or polysubstituted by at least one substituent selected from the group of OH, O—C(O)—$R^1$, $CH_2OH$, $CO_2H$, $CO_2R^1$, $R^5$, the $R^3$ radical is selected from the group consisting of branched or unbranched $C_1$- to $C_{60}$-alkyl radicals, branched or unbranched $C_2$- to $C_{60}$-alkenyl radicals, $C_7$- to $C_{60}$-arylalkyl radicals and/or $C_6$- to $C_{60}$-heteroarylalkyl radicals, where these are unsubstituted or mono- or polysubstituted by at least one substituent selected from the group of OH, $CH_2OH$, $CH_2$—$R^4$, the $R^4$ radical has the following structure (II):

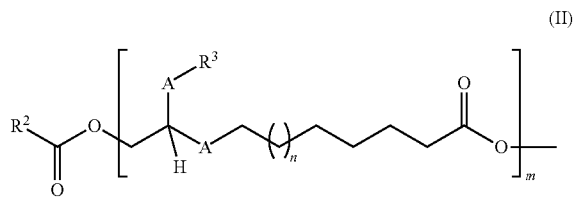

where the $R^2$, $R^3$ and A radicals and the numbers m and n present therein are defined as described above, the $R^5$ radical has the following structure (III):

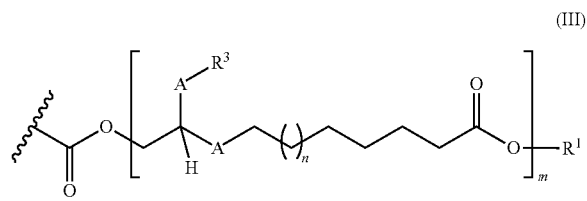

where the $R^1$, $R^3$ and A radicals and the numbers m and n present therein are defined as described above.

In addition, mixtures containing at least two compounds having the general structure (I) are also provided, where two of these compounds in each case are regioisomers of one another. These pairs of regioisomers result from the simultaneous introduction of the hydroxymethyl function in, for example, the 9 and 10 position in the case of the hydroformylation of the double bond in the 9,10 position. Subsequently, proceeding from such a "regioisomer pair", it is alternatively possible to prepare mixtures, the different "m". These compounds in turn, by comparison, are no longer all regioisomers of one another.

By contrast with the known estolide compounds having the structure Lit-1 shown in FIG. 1, the inventive compounds having the general structure (I) have an additional "methylene bridge" (methylene unit, —($CH_2$)—) between the carbon of the fatty acid chain and the oxygen of the C—O single bond of the adjacent ester group. This "methylene bridge" opens up additional options with regard to changes in conformation of the respective molecules and can thus contribute to higher steric flexibility, combined with correspondingly advantageous product properties. This also opens up the option of novel product properties by comparison with other rigid lubricants, for example the estolide compounds. By contrast with the estolide compounds which, according to the description, is prepared by linkage of multiple unsaturated fatty acids as a result of uncontrolled addition of the carboxylic acid unit of an unsaturated fatty acid with the alkene unit of a further unsaturated fatty acids and correspondingly leads to mixtures of compounds of different chain length, the controlled preparation of compounds of a particular chain length is possible with the aid of the process of the invention, where these take the form of regioisomers. This selective synthesis of compounds of different chain length and the presence thereof in isolated form enables later controlled "blending", i.e. the mixing of compounds of different chain length tailored to the desired individual use for achievement of the desired lubricant properties. The individual representatives of the compounds of the invention thus form a modular "building block system", which can then be used in a controlled manner for specific lubricant applications.

DESCRIPTION OF THE FIGURES

FIG. 7 is a diagram of compounds of the general structure (Ib) prepared from 1,6-hexanediol as a diol component.

FIG. 8 is a diagram of compounds of the general structure (Ic) prepared from n-hexanedicarboxylic acid as a dicarboxylic acid component.

DETAILED DESCRIPTION

Particularly preferred representatives of the inventive compounds of the general formula (I) include those compounds that can be prepared proceeding from the unsaturated fatty acids oleic acid, linoleic acid, linolenic acid, erucic acid, nervonic acid, gadoleic acid and other ω-n-fatty acids.

Figure 1:
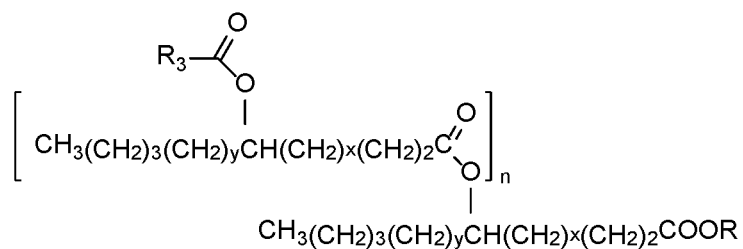
FIG. 1 is a diagram of the general structure of estolide compounds of the prior art.
Figure 2:
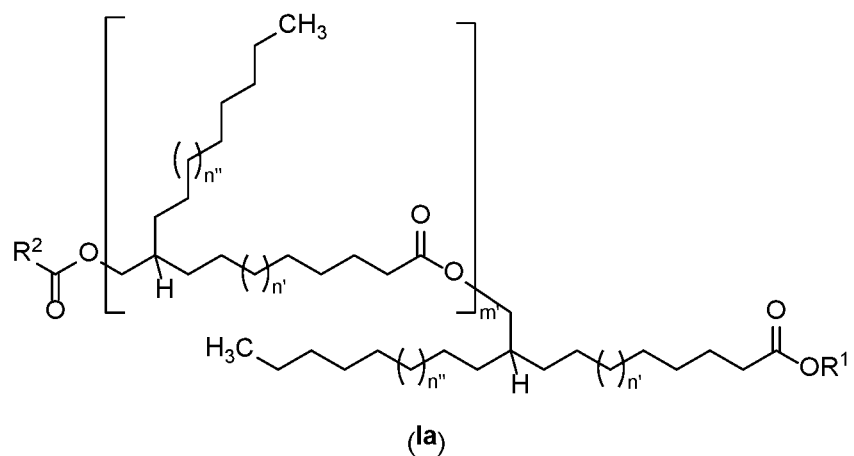
FIG. 2 is a diagram of the structure of compounds using oleic acid derivatives (Ia) according to the present disclosure.

One illustrative compound type of these particularly preferred representatives of the inventive compounds having the general structure (I) is that of the oleic acid-derived compounds of the general structure (Ia) that are illustrated in FIG. 2, where m' is 1 to 5, n' and n" are either 1 and 2 or 2 and 1, and $R^1$ and $R^2$ have definitions described above.

Figure 3:
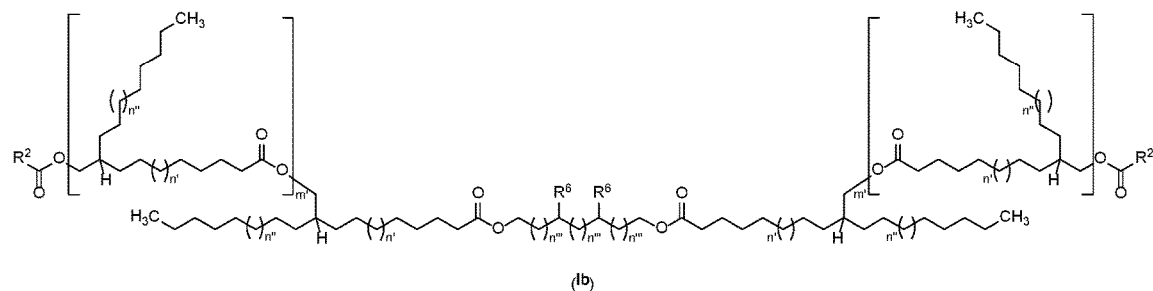
FIG. 3 is a diagram of the structure of compounds using oleic acid derivatives (Ib) according to the present disclosure.

A further compound type of the particularly preferred representatives of the inventive compounds having the general structure (I) is that of the oleic acid-derived compounds having "diol bridges" of the general structure (Ib) that are shown in FIG. 3, where m' is 0 to 5, n' and n" are either 1 and 2 or 2 and 1, n'" is 0 to 10, $R^1$ and $R^2$ have the definitions described above and the $R^6$ radical is selected from the group consisting of branched or unbranched $C_1$- to $C_{60}$-alkyl radicals and branched or unbranched $C_2$- to $C_{60}$-alkenyl radicals. In the case that m'=1 to 5, the $R^2$ radical is additionally selected from the group consisting of branched or unbranched $C_2$- to $C_{60}$-alkenyl radicals or methyl radical, where this is unsubstituted or mono- or polysubstituted by at least one substituent selected from the group of OH, O—C(O)—$R^1$, $CH_2OH$, $CO_2H$, $CO_2R^1$, $R^5$.

Figure 4:
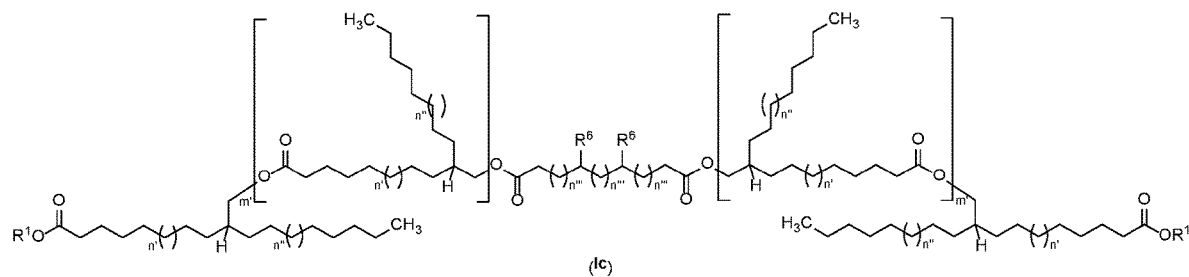
FIG. 4 is a diagram of the structure of compounds using oleic acid derivatives (Ic) according to the present disclosure.

An alternative further illustrative compound type of the particularly preferred representatives of the inventive compounds having the general structure (I) is that of the compounds having "dicarboxylic acid bridges" of the general structure (Ic) that are shown in FIG. 4, where m' is 0 to 5, n' and n" are either 1 and 2 or 2 and 1, n'" is 0 to 10, $R^1$ and $R^2$ have definitions described above and the $R^6$ radical is selected from the group consisting of branched or unbranched $C_1$- to $C_{60}$-alkyl radicals and branched or unbranched $C_2$- to $C_{60}$-alkenyl radicals. In the case that m'=1 to 5, the $R^2$ radical is additionally selected from the group consisting of branched or unbranched $C_2$- to $C_{60}$-alkenyl radicals or methyl group, where this is unsubstituted or mono- or polysubstituted by at least one substituent selected from the group of OH, O—C(O)—$R^1$, $CH_2OH$, $CO_2H$, $CO_2R^1$, $R^5$.

The novel inventive compounds of type (I) can be prepared in various ways, and two preferred embodiments are described below. These syntheses differ considerably from those preparation methods that lead to other lubricant compounds, for example by comparison with the processes for preparing the estolide compounds, by way of which the compounds of the invention are typically unobtainable.

Both preferred embodiments of the synthesis of the inventive compounds of type (I) proceed from unsaturated fatty acid as starting compound. More particularly, oleic acid, linoleic acid, linolenic acid, erucic acid and nervonic acid, gadoleic acid and other ω-n-fatty acids are used here. The use of renewable raw materials as starting compounds is advantageous here from the perspective of economy and sustainability.

There are different embodiments for each of the two abovementioned preferred synthesis strategies. More particularly, it is possible to vary the sequence of the reaction steps involved in any way.

The two abovementioned preferred synthesis strategies are described in detail hereinafter.

In the first preferred embodiment, the process of the invention proceeds from an unsaturated fatty acid which is first esterified, or the corresponding ester is used directly. This esterified product is then subjected to a hydroformylation reaction in the presence of molecular hydrogen ($H_2$) and carbon monoxide (CO) and, after subsequent hydrogenation, which is preferably effected in situ, the corresponding methylol-substituted derivative is obtained. These steps for hydroformylation of unsaturated fatty acids and the subsequent hydrogenation thereof to give the corresponding methylol-substituted derivative have been described many times in the literature, for example in R. Lai, M. Naudet, E. Ucciani, *Rev. Fr. Corps Gras* 1966, 13, 737-745, R. Lai, M. Naudet, E. Ucciani, *Rev. Fr. Corps Gras* 1968, 15, 5-21, R. Lai, E. Ucciani, M. Naudet, *Bull. Soc. Chim. Fr.* 1969, 793-797, E. N. Frankel, *J. Am. Oil Chem. Soc.* 1971, 48, 248-253, E. N. Frankel, F. L. Thomas, *J. Am. Oil Chem. Soc.* 1972, 49, 10-14, J. P. Friedrich, G. R. List, V. E. Sohns, *J. Am. Oil Chem. Soc.* 1973, 50, 455-458, E. H. Pryde, *J. Am. Oil Chem. Soc.* 1984, 61, 419-425, E. H. Pryde, *J. Am. Oil Chem. Soc.* 1984, 61, 419-425 and E. Benetskiy, S. Lühr, M. Vilches-Herrera, D. Selent, H. Jiao, L. Domke, K. Dyballa, R. Franke, A. Börner, *ACS Catal.* 2014, 4, 2130-2136.

Review articles on this topic that are additionally available to the person skilled in the art include, for example, the contributions by E. H. Pryde, E. N. Frankel, J. C. Cowan, *J. Am. Oil Chem. Soc.* 1972, 49, 451-456, E. N. Frankel, *Ann. N.Y. Acad. Sci.* 1973, 214, 79-93, J. W. E. Coenen, *Fette, Seifen, Anstrichmittel* 1975, 77, 461-467, E. N. Frankel, E. H. Pryde, *J. Am. Oil Chem. Soc.* 1977, 54, 873A-881A, E. H. Pryde, *J. Am. Oil Chem. Soc.* 1979, 56, 719A-725A.

The hydroxyl group of the resultant methylol-substituted derivative is then esterified again, which can be effected directly with a non-hydroxyl-substituted fatty acid, for example, or with another long-chain alkanecarboxylic acid having at least one hydroxyl group (or ester thereof in a transesterification reaction). This long-chain alkanecarboxylic acid having at least one hydroxyl group is preferably a long chain fatty acid which bears at least one hydroxymethyl group and can be prepared, for example, in the manner outlined above. For the esterification of the hydroxyl group for preparation of the dimers or oligomers, it is possible to use either the respective acids directly or activated acid derivatives, e.g. acid chlorides and anhydrides, or acid esters (for a transesterification reaction). It is also possible to use dicarboxylic acids, tricarboxylic acids and higher carboxylic acids or derivatives thereof.

In detail, the first preferred embodiment of the process of the invention for preparing inventive ester compounds of the general formula (I) comprises the following steps:

(A) proceeding from an unsaturated fatty acid or an ester derived therefrom having the general formula (IV)

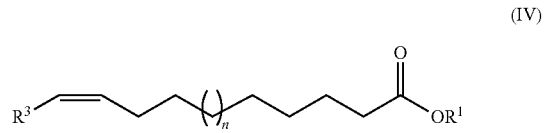

(IV)

where $R^1$, $R^3$ and n are as defined above, a hydroformylation is conducted to form compounds having the general formula (V)

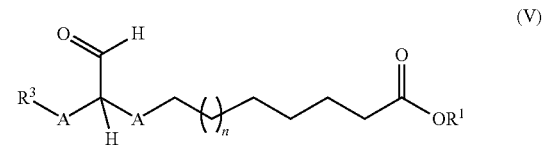

(V)

where $R^1$, $R^3$, A and n are as defined above, and (B) the compounds obtained having the general formula (V) are subsequently converted by hydrogenation to the compounds having the general formula (VI)

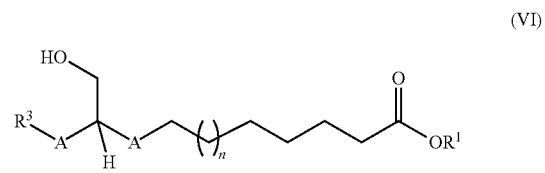

(VI)

where $R^1$, $R^3$, A and n are as defined above, and (C) then an ester formation reaction is conducted using an acyl donor having the formula (VII)

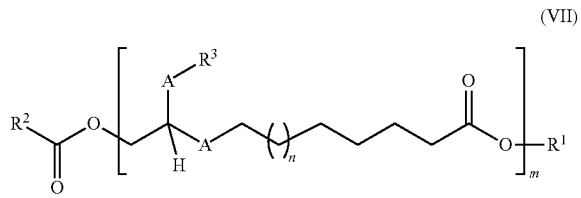

(VII)

where $R^1$, $R^2$, $R^3$, A and n and m are as defined above, giving the inventive compounds of the general formula (I)

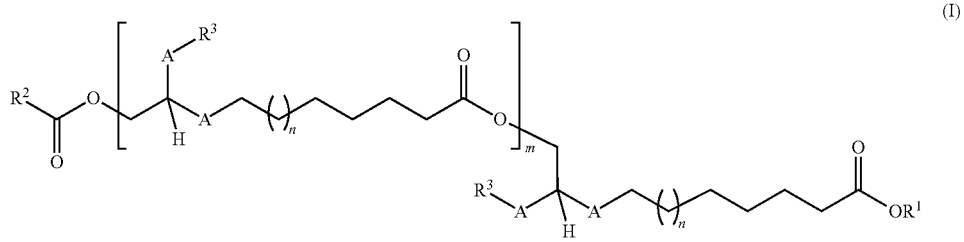

(I)

where $R^1$, $R^2$, $R^3$, A and n and m are as defined above. Optionally, there can subsequently be an exchange of the $R^1$ group by an esterification or transesterification reaction. Likewise optionally, in the case of a free hydroxyl group in the $R^2$ radical, further esterification thereof is possible.

This first preferred embodiment is additionally presented or illustrated hereinafter using the example of preparation of corresponding inventive compounds proceeding from oleic acid as an illustrative representative of an unsaturated fatty acid as starting compound. This synthesis route is additionally summarized in the form of a diagram in FIG. 5.

Figure 5:
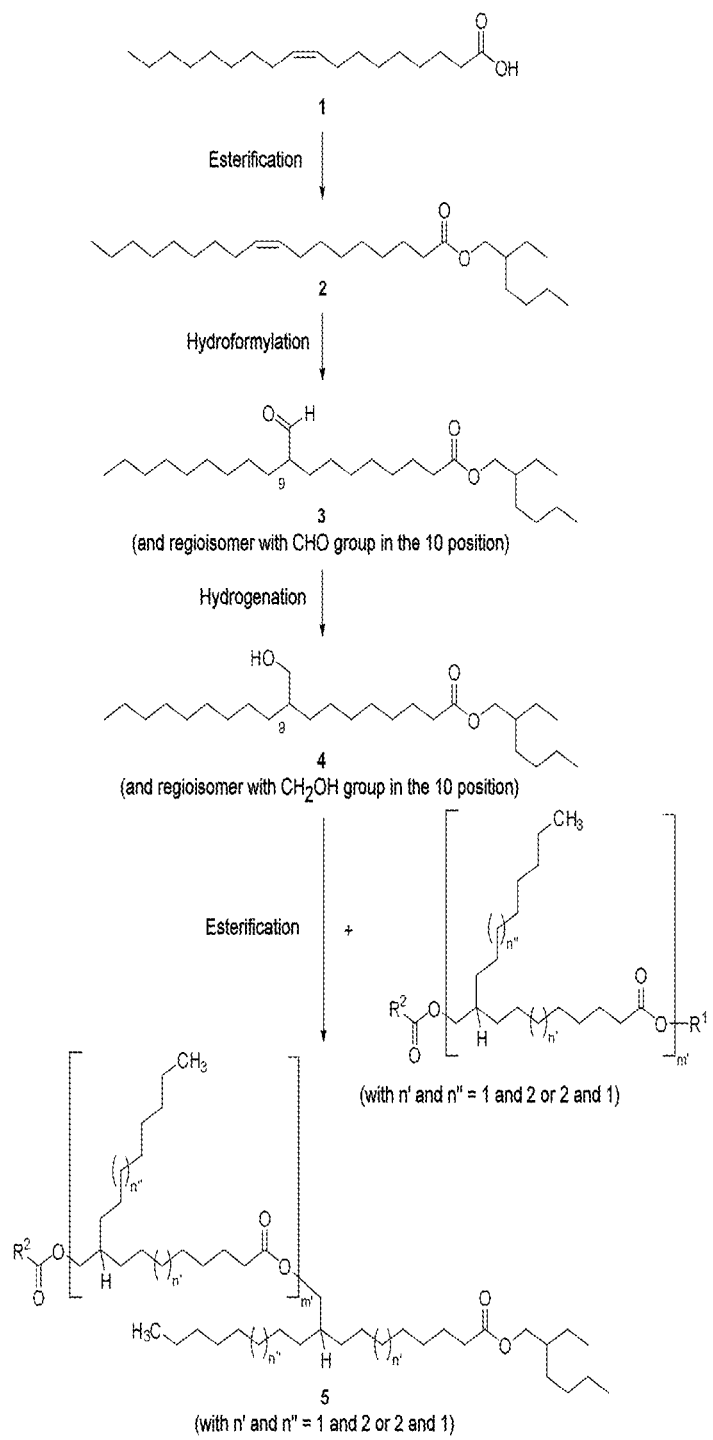
FIG. 5 is a diagram of the steps for synthesizing a hydroformylation from oleic acid according to one aspect of the present disclosure.

Proceeding from oleic acid 1 as a starting compound readily obtainable from a renewable raw material, there is firstly an esterification reaction, wherein, in the illustrative example, 2-ethylhexan-1-ol is used as a readily available bulk chemical obtainable in large volumes (FIG. 5). For the esterification, there is generally a broad spectrum of methods available to the person skilled in the art, one attractive synthesis option being catalytic methods using acids or biocatalysts, preferably a lipase.

The ester 2 obtained in the esterification reaction is subsequently subjected to a hydroformylation reaction, which gives rise to the compound 3 substituted by a CH(=O)— radical in the 9 position (in a mixture with the regioisomer substituted by a CH(=O)— radical in the 10 position). The subsequent hydrogenation of the carbonyl group in 3 then affords the 9-methylol-substituted oleic ester 4 (in a mixture with the 10-methylol-substituted regioisomer), which is subsequently converted to the desired target compounds 5 by acylating the hydroxyl group.

The reaction steps of hydroformylation and hydrogenation can be combined in such a way that, after the hydroformylation, the subsequent hydrogenation of the aldehyde group to give the methylol-substituted derivative 4 is effected directly in situ. The hydroxymethyl group (methylol group) formed in the hydroformylation may, owing to the typically low or not very pronounced regioselectivity of the hydroformylation reaction, be either in the 9 or 10 position and may typically contain a mixture of the two isomers. For reasons of clarity, FIG. 5 shows only the 9-substituted isomer in the diagram. In the products of type 5 formed, compounds with m'=0 or 1 to 5 are particularly preferred.

Alternatively, the target compounds can also be prepared by way of a second, preferred embodiment by a route described hereinafter. In this case, an unsaturated fatty acid is first reacted with formaldehyde (or a formaldehyde derivative, for example paraformaldehyde) in an ene reaction, optionally a subsequent reduction of the resulting C=C bond (for example via a heterogeneously catalyzed hydrogenation), and followed by a subsequent esterification. Here too, the sequence can be varied and can first be commenced, for example, with the esterification, followed by the ene reaction and subsequent esterification. For the esterification of the hydroxyl group for preparation of the dimers or oligomers, it is possible to use either carboxylic acids directly or activated carboxylic acid derivatives, for example carbonyl chlorides and anhydrides, or carboxylic esters (for a transesterification reaction). It is also possible to use dicarboxylic acids, tricarboxylic acids and higher carboxylic acids or derivatives thereof.

The step of the ene reaction proceeding from an unsaturated fatty acid and formaldehyde (or a formaldehyde derivative, for example paraformaldehyde) to form the hydroxymethyl-substituted unsaturated fatty acid derivative products with the trans-C=C double bond in the adjacent position to the hydroxymethyl substituent has already been described in the literature, for example in U. Biermann, J. Metzger, *Fat. Sci. Technol.* 1991, 93, 282-284 and J. Metzger, U. Biermann, *Synthesis* 1992, 5, 463-465, and so the person skilled in the art, in the selection of the reaction conditions, can be guided by these described studies. For example, in U. Biermann, J. Metzger, *Fat. Sci. Technol.* 1991, 93, 282-284, in the reaction of oleic acid as fatty acid with paraformaldehyde (2.3 equivalents), $Me_2AlCl$ is also used as a Lewis acid added in stoichiometric amounts at likewise 2.3 equivalents. The ene reaction with different substrates has already been reported before, including in B. Snider, D. Rodini, T. Kirk, R. Cordova, *J. Am. Chem. Soc.* 1982, 104, 555-563, and so the person skilled in the art, in the choice of reaction conditions, is also able to consult the reaction conditions described in these studies.

In detail, this second preferred embodiment of the process of the invention for preparing inventive ester compounds of the general formula (I) comprises the following steps:
  (A) proceeding from an unsaturated fatty acid or an ester derived therefrom having the general formula (IV)

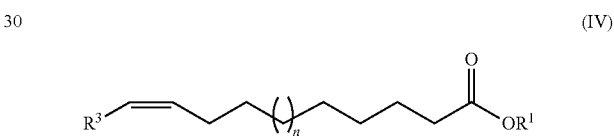

(IV)

where $R^1$, $R^3$ and n are as defined above,
an ene reaction and subsequent optional hydrogenation of the resultant C=C double bond is conducted to form compounds having the general formula (VI)

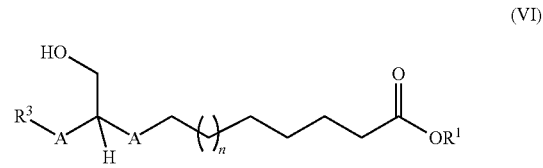

(VI)

where $R^1$, $R^3$, A and n are as defined above, and
(B) the compounds having the general formula (VI) obtained are then subjected to an ester formation reaction using an acyl donor having the formula (VII)

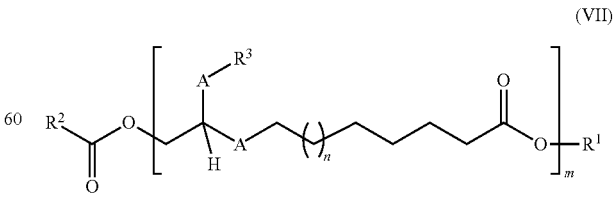

(VII)

where $R^1$, $R^2$, $R^3$, A and n and m are as defined above, giving inventive compounds of the general formula (I)

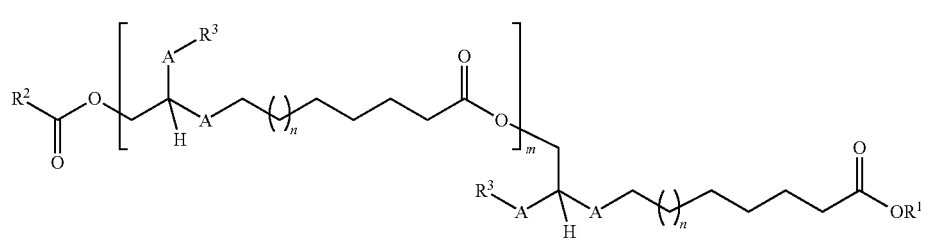

(I)

where R[1], R[2], R[3], A and n and m are as defined above.

Optionally, there can subsequently be an exchange of the R[1] group by an esterification or transesterification reaction. Likewise optionally, in the case of a free hydroxyl group in the R[2] radical, further esterification thereof is possible.

The second embodiment is presented and illustrated hereinafter using the example of the preparation of the respective inventive compounds proceeding from oleic acid as illustrative representative of an unsaturated fatty acid as starting compound. This example is additionally summarized in the form of a diagram in FIG. 6. In this case, the reaction sequence of the individual steps involved can be varied, so as to result in embodiments A and B described hereinafter among others.

Figure 6:
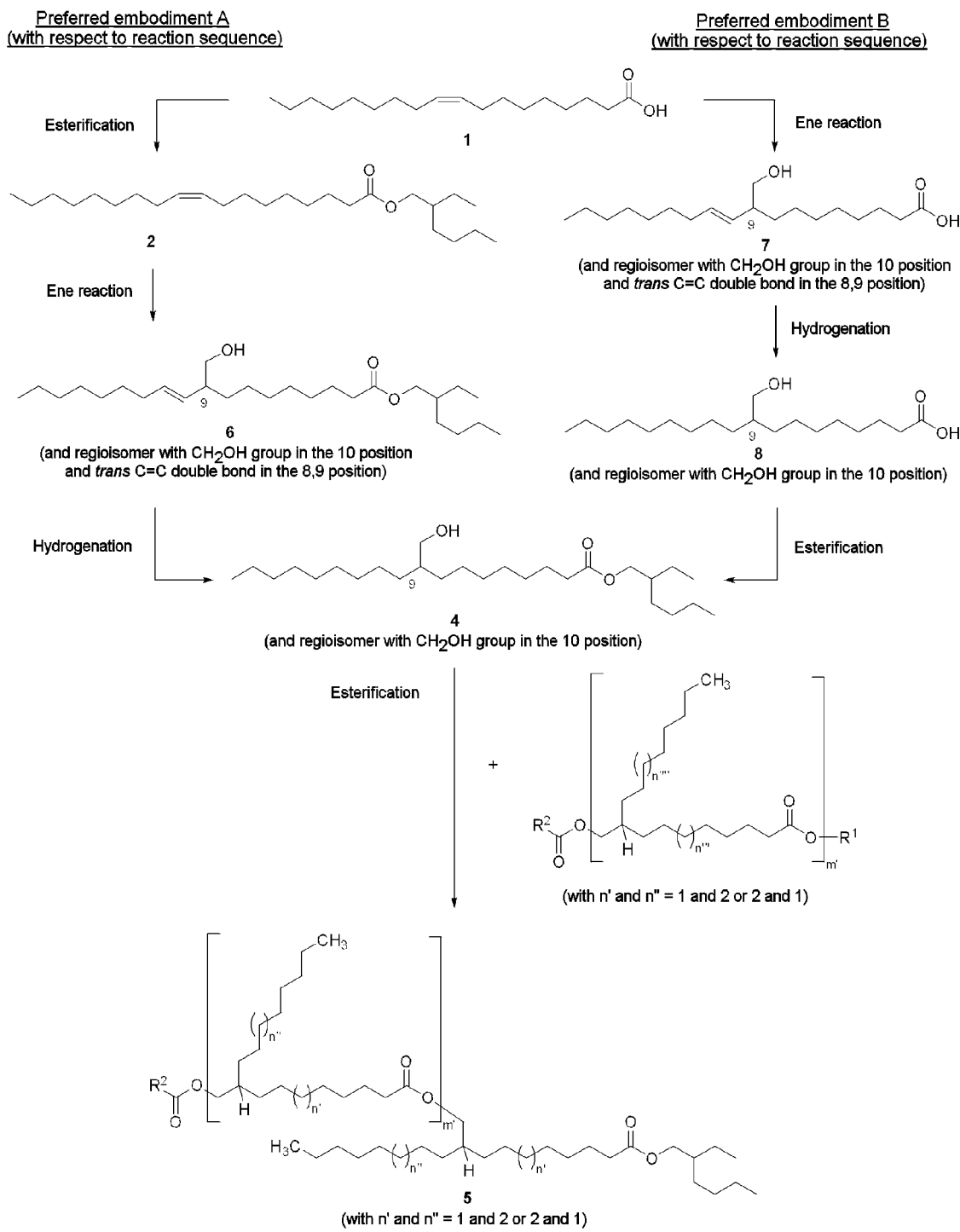
FIG. 6 is a diagram of synthesizing strategies proceeding from oleic acid with the incorporation of an ene reaction according to a further aspect of the present disclosure.

Proceeding from oleic acid 1, in embodiment A, an esterification reaction is first effected, wherein, in the illustrative example, 2-ethylhexan-1-ol is used as a readily available bulk chemical obtainable in large volumes. As already stated above, there is generally a broad spectrum of methods available to the person skilled in the art for the esterification, and one attractive synthesis option is catalytic methods using acids or biocatalysts, preferably a lipase. The ester 2 obtained in the esterification reaction is then subjected to an ene reaction with paraformaldehyde in the presence of a Lewis acid, giving rise to the hydroxymethyl-substituted unsaturated fatty acid derivative 6 containing a trans C=C double bond in the adjacent position to the hydroxymethyl substituent (for example, the double bond in the case of introduction of the hydroxymethyl function in the 9 position is then in the 10,11 position) (FIG. 6). The subsequent hydrogenation of this C=C double bond (alkene unit) adjacent to the methylol group in 6 then affords the saturated methylol-substituted oleic ester 4, which is subsequently converted to the desired target compounds of type 5 by acylating the hydroxyl group.

The hydroxymethyl group formed in the ene reaction may, owing to the low or not very pronounced regioselectivity of the ene reaction, be either in the 9 or 10 position with corresponding positioning of the trans C=C double bond in the 10,11 position (in the case of the 9 position of the hydroxymethyl group) or in the 8,9 position (in the case of the 10 position of the hydroxymethyl group). Typically, a mixture of the two isomers is contained. For reasons of clarity, FIG. 6 shows only the 9-hydroxymethyl-substituted isomer with the trans C=C double bond in the 10,11 position in the diagram. In the case of the products of type 5 formed, particular preference is given to compounds with m'=0 or 1 to 5.

Optionally, the C=C double bonds resulting from the ene reaction can also be hydrogenated only as a final stage after initial oligomerization. Furthermore, it is optionally additionally possible generally to dispense with one or more of the hydrogenation steps, in which case the resulting products have at least one double bond.

In the likewise preferred embodiment B, by comparison with embodiment A, the reaction sequence is altered (FIG. 6). For instance, first of all, directly proceeding from oleic acid 1, an ene reaction is effected to obtain the compound 7, which is subsequently converted to the intermediate 4 by way of a hydrogenation of the trans C=C double bond and subsequent esterification. Optionally and alternatively, it is also possible first to esterify the compound 7 (which would form the compound 6) and closingly to hydrogenate it, likewise giving the compound 4. In this case too of the ene reaction proceeding from 1, the hydroxymethyl group formed in compound 7, owing to the low or not very marked regioselectivity of the ene reaction, may be either in the 9 or 10 position with corresponding positioning of the trans C=C double bond in the 10,11 position (in the case of the 9 position of the hydroxymethyl group) or in the 8,9 position (in the case of the 10 position of the hydroxymethyl group). Typically, a mixture of the two isomers is contained. For reasons of clarity, FIG. 6 shows only the 9-hydroxymethyl-substituted isomer with a trans C=C double bond in the 10,11 position in the diagram. The compound 4 is then, as already described above in embodiment A, converted to the desired target compounds of type 5, particular preference being given to compounds with m'=0 or 1 to 5.

An illustrative representative of the preferred compound class (Ib) is the mixture described hereinafter of the three by esterification of the mixture described in example 9 cited hereinafter of two regioisomers with 1,6-n-hexanediol as (di)alcohol component (FIG. 7). Since 1,6-n-hexanediol is a diol and can thus be diesterified and, at the same time, both the 9-substituted and the 10-substituted regioisomer of the ester mixture prepared in example 9 can react with 1,6-n-hexanediol, this gives rise to a mixture of 3 regioisomers (by involvement of two 9-substituted regioisomers or two 10-substituted regioisomers or one 9-substituted regioisomer and one 10-substituted regioisomer in such a transesterification reaction), which is shown in FIG. 7 below. For better illustration, the molecular fragment that originates from 1,6-n-hexanediol in each case is shown in a box. Alternatively, such representatives of compound class (Ib) can also be prepared by the transesterification proceeding from simple alkyl esters (such as methyl and ethyl esters) or directly proceeding from the corresponding carboxylic acids by an esterification reaction.

One illustrative representative of the preferred compound class (Ic) is that of the mixture described hereinafter of the three by esterification of the mixture of two regioisomers described in example 8 below with n-hexanedicarboxylic acid as (di)carboxylic acid component (FIG. 8). Since n-hexanedicarboxylic acid is a dicarboxylic acid and can thus be diesterified and, at the same time, both the 9-substituted and the 10-substituted regioisomer of the ester mixture prepared in example 8 can react with n-hexanedicarboxylic acid, this then gives rise to a mixture of 3 regioisomers (by involvement of two 9-substituted regioisomers or two 10-substituted regioisomers or one 9-substituted regioisomer and one 10-substituted regioisomer in such a transesterification reaction), which is shown in FIG. 8 below. For better illustration, the molecular fragment that originates from n-hexanedicarboxylic acid in each case is shown in a box. Alternatively, such representatives of compound class (Ic) can also be prepared by transesterification proceeding from analogous O-acylated compounds with structurally simpler acyl components (for example acetyl, propanoyl) or directly proceeding from the corresponding non-O-acylated compounds with a free hydroxymethyl group by an esterification reaction.

Figure 9:
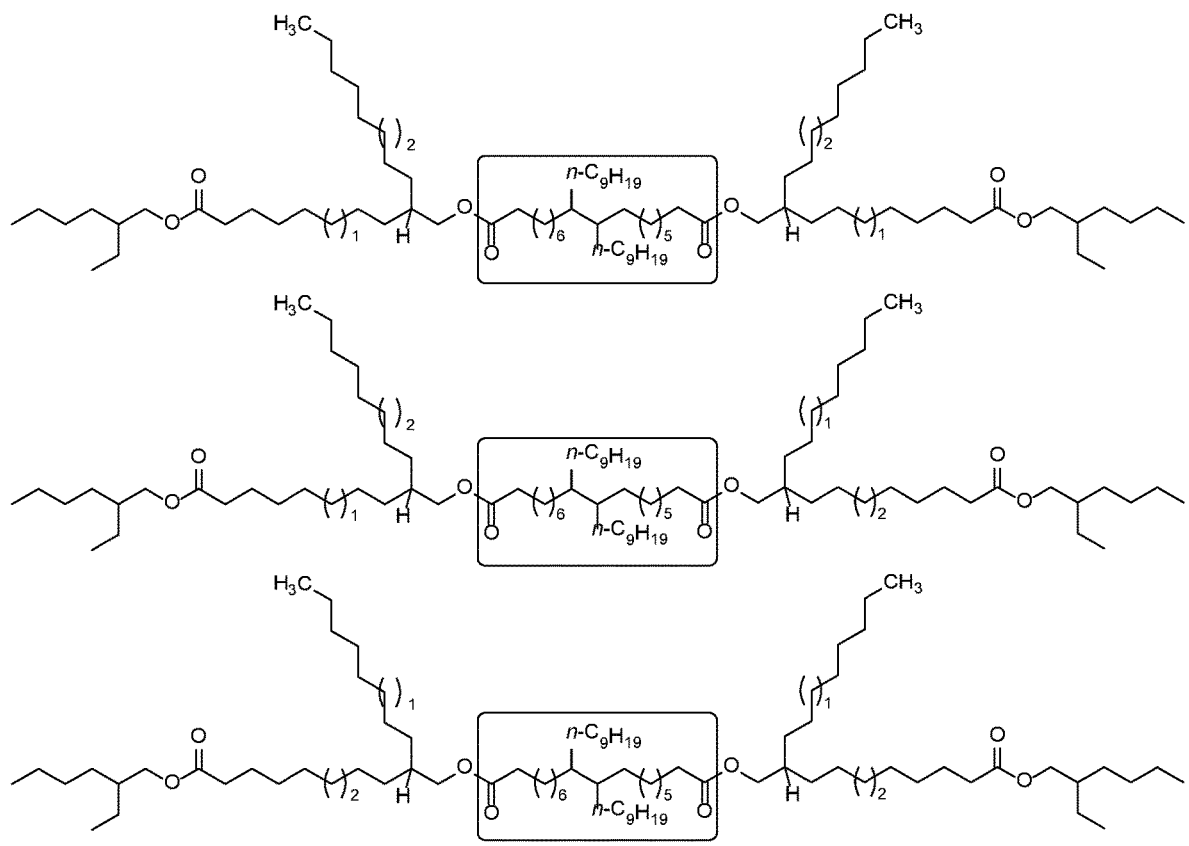
FIG. 9 is a diagram of compounds of the general structure (Ic) prepared from dicarboxylic acid Pripol 1013 as a dicarboxylic acid component.

In addition, a representative of this compound class (Ic) is the mixture, described in example 13 below, of the regioisomers corresponding to the general structure (Ic) that are present therein, which are formed from the esterification reaction of the mixture of the invention described in example 8 with the dicarboxylic acid Pripol 1013 from Croda GmbH (FIG. 9). For better illustration, the molecular fragment originating from the commercial dicarboxylic acid Pripol 1013 in each case is shown in a box.

As well as n-hexanedicarboxylic acid and dimer acid (Pripol 1013), further polybasic carboxylic acids and carboxylic anhydrides are used, especially hydrogenated dimer acid, hydrogenated or unhydrogenated trimer acids, terephthalic acid, isophthalic acid, phthalic acid, trimellitic acid, hemimellitic acid, trimesic acid, citric acid, itaconic acid, oxalic acid, 2,2'-thiodiacetic acid, 3,3'-thiodipropionic acid, admergic acid, 2,5-furandicarboxylic acid, cyclohexane-1,4-dicarboxylic acid, cyclohexane-1,2-dicarboxylic acid, cyclohexene-4,5-dicarboxylic acid, phenylsuccinic acid, glutamic acid, aspartic acid, ethylenediaminetetraacetic acid, diethylenetriaminepentaacetic acid, propylenediaminetetraacetic acid, nitrilotriacetic acid, diglycolic acid and iminodiacetic acid and derivatives thereof.

A further characteristic feature of the process of the invention is the inclusion of the reaction type of esterification within the scope of the preferred embodiments of the process proceeding from unsaturated fatty acids and the synthesis sequences employed here. Various options are available to the person skilled in the art for the esterification of hydroxyl groups. For instance, either the acids required may be used directly, or activated acid derivatives derived therefrom may be used, e.g. acid chlorides and anhydrides, or acid esters (for a transesterification reaction). A particularly attractive synthesis option here is that of catalytic methods which permit direct esterification proceeding from alcohol and acid component without the need to use activated carboxylic acid derivatives such as carbonyl chlorides and anhydrides. Such catalytic methods are known with involvement both of chemocatalysts and biocatalysts and are described, for example (with particular focus on biocatalysts), in G. Hills, Eur. J. Lipid Sci. Technol. 2003, 105, 601-607, O. Thum, K. M. Oxenbøll, SOFW J. 2008, 134, 44-47, L. Hilterhaus, O. Thum, A. Liese, Org. Process Res. Dev. 2008, 12, 618-625 and M. B. Ansorge-Schumacher, O. Thum, Chem. Soc. Rev. 2013, 42, 6475-6490. The use of biocatalysts is particularly attractive here since it is possible to conduct esterification reactions in a highly efficient manner under mild reaction conditions. Correspondingly, the preparation of the inventive compounds of the general formula (I) in a synthesis method in which a biocatalyst selected from the enzyme class of the hydrolases is used for at least one of the esterification reactions involved is a particularly preferred embodiment. Particularly suitable biocatalysts from the enzyme class of the hydrolases for the process of the invention are lipases, and the commercially available lipase from Candida antarctica B is a particularly suitable lipase component.

For the synthesis methods that lead to the inventive compounds of the general formula (I), various possible options are available to the person skilled in the art in the choice of reaction conditions, these being described in detail in the literature for the individual reaction types involved. Among other parameters, the person skilled in the art is free to choose the respective reaction media and may make use, for example, of a broad spectrum of solvents for performance of the synthesis reactions in the process of the invention. However, it is particularly advantageous with regard to the sustainability of the preparation process to avoid solvents. Especially for esterification reactions, solvent-free syntheses have already been described as efficient in the literature, for example in the already above-cited contributions G. Hills, Eur. J. Lipid Sci. Technol. 2003, 105, 601-607, O. Thum, K. M. Oxenbøll, SOFW J. 2008, 134, 44-47, L. Hilterhaus, O. Thum, A. Liese, Org. Process Res. Dev. 2008, 12, 618-625 and M. B. Ansorge-Schumacher, O. Thum, Chem. Soc. Rev. 2013, 42, 6475-6490. Since the reaction type of esterification is also a characteristic feature of the process of the invention, the preparation of the inventive compounds of the general formula (I) in a synthesis method in which at least one of the esterification reactions involved is effected under solvent-free reaction conditions is a particularly preferred embodiment.

A particular technical advantage of the process of the invention developed and of the products having an O-acylated methylol function thus obtained is the presence of a primary alcohol function in the parent hydroxymethylol-substituted fatty acid esters as substrate. This functional primary amino group is highly suitable for enzyme-catalytic reactions under mild preparation conditions and at low temperatures, and hence enables the preparation of the desired compounds under environmentally friendly conditions with simultaneously low energy consumption.

A further general technical advantage of the compounds of the invention and of the preparation process of the invention lies in the enormously high selectivity. The estolide compounds disclosed in DE 698 35 694 T2 cannot be prepared in this selectivity since the reaction linkage here proceeds from an unsaturated fatty acid as base unit by addition of the fatty acid unit of this base unit onto the alkene unit of the next base unit, and hence di-, tri-, tetra- or generally oligomers and even polymers are formed as a mixture. In the process of the invention, by virtue of mild reaction conditions and highly selective enzyme reactions, but also by virtue of the strategy of the reaction regime, preferably only monofunctionalization of the methylol component of the starting compound is achieved in each case (said starting compound consisting, for example, of a mixture of a 9- and 10-methylol-substituted fatty acid ester). Furthermore, the tailored preparation of more highly substituted trimers and tetramers is also conceivable in a selective manner by correspondingly controlled syntheses. Therefore, the target compounds are obtained with high selectivity in defined form with avoidance of higher oligomeric or polymeric structures, in a way which is not possible with the known methods, by which complex product mixtures are obtained.

The inventive ester compounds of the general formula (I) are of excellent suitability for use in lubricant compositions and are suitable for use both in the high-temperature sector and in the marine sector, and as lubricant which is used in the foods sector.

As well as the novel ester compounds, the lubricant compositions of the invention may especially contain further base oil components, especially based on natural glyceride esters and fatty acids, preferably sunflower oil, rapeseed oil or colza oil, linseed oil, corn oil or corn germ oil, safflower oil, soybean oil, linseed oil, groundnut oil, "lesquerella" oil, palm oil, olive oil, in the monomeric, oligomeric and/or polymerized forms or mixtures of the oils mentioned.

In addition, the lubricant compositions of the invention, as well as the novel ester compounds, may contain further esters such as trimethylolpropane and pentaerythritol esters, and also TMP complex esters, in fully or partly esterified form with saturated and/or mono- or polyunsaturated carboxylic acids of chain length C6-C36, where these may be linear or branched, complex esters of dimer acids, dimer acid esters such as ethylhexyl dimerate, aliphatic carboxylic and dicarboxylic esters, and also phosphate esters, trimellitic and pyromellitic esters, ethers, polyether polyols and perfluoropolyethers, alkyl diphenyl ethers and polyphenyl ethers, silicone oils, polyglycols consisting of randomly distributed polyoxyethylene and/or polyoxypropylene units and/or other polyoxyalkylene units, and other glycol derivatives, polyalphaolefins including those prepared by metallocene catalysis, and alpha-olefin copolymers, polymeric systems, for example unhydrogenated, partly hydrogenated or fully hydrogenated polyisobutylene or a mixture thereof, styrene and polystyrene and their derivatives and/or polymeric systems based on acrylates, acetate polymers and amides, polyethylenes, polypropylenes, halogenated polypropylenes and/or cycloalkanes, mineral oils, for example white oil, alkylated diphenyl ethers, alkylated naphthalenes and perfluoropolyethers.

The lubricant containing the inventive ester compound of the general formula (I) may be used either in the form of a lubricant oil or a lubricant grease.

The lubricant further comprises additives that may be used individually or in combination and are selected from the group consisting of anticorrosion additives, antioxidants, antiwear additives, UV stabilizers, inorganic or organic solid lubricants, pour point and VI improvers, polymers, adhesion additives, dyes, emulsifiers, defoamers and solid lubricants that are typical for the formulation of a lubricant oil or lubricant grease.

Lubricant greases may be produced with different thickeners. One possible group of thickeners is that of ureas consisting of the reaction product of a diisocyanate, preferably 2,4-diisocyanatotoluene, 2,6-diisocyanatotoluene, 4,4'-diisocyanatodiphenylmethane, 2,4'-diisocyanatophenylmethane, 4,4'-diisocyanatodiphenyl, 4,4'-diisocyanato-3,3'-dimethylphenyl, 4,4'-diisocyanato-3,3'-dimethylphenylmethane, which may be used individually or in combination, with an amine of the general formula R'$_2$—N—R, or a diamine of the general formula R'$_2$—N—R—NR'$_2$, where R is an aryl, alkyl or alkylene radical having 2 to 22 carbon atoms and R' is identical or different and is a hydrogen, an alkyl, alkylene or aryl radical, or with mixtures of amines and diamines, or as thickener a representative is selected from the group of the Al complex soaps, simple metal soaps of the elements of the first and second main groups of the Periodic Table, complex metal soaps of the elements of the first and second main groups of the Periodic Table, bentonites, sulfonates, silicates, aerosil, polyimides or PTFE or a mixture of the aforementioned thickeners.

In order to meet the legal requirements with regard to the use of lubricants for lubrication of machinery for the processing of foods, it is appropriate when the additives used have an H1 classification.

The addition of antioxidants can reduce or even prevent the oxidation of the oil or grease of the invention, especially in use. Correspondingly, the addition of antioxidants is a further preferred embodiment of the process of the invention. The antioxidants are selected from the group consisting of diaromatic amines, phenol resins, thiophenol resins, phosphites, butylated hydroxytoluene, butylated hydroxyanisole, phenyl-α-naphthylamines, phenyl-β-naphthylamines, octylated/butylated diphenylamines, di-α-tocopherol, di-tert-butyl-phenyl, benzenepropanoic acid and mixtures of these components.

The lubricant of the invention may contain anticorrosion additives, metal deactivators or ion complexing agents. These include triazoles, imidazolines, N-methylglycine (sarcosine), benzotriazole derivatives, N,N-bis(2-ethylhexyl)-ar-methyl-1H-benzotriazole-1-methanamine; N-methyl-N-(1-oxo-9-octadecenyl)-glycine, mixture of phosphoric acid and its mono- and diisooctyl esters with (C11-14)-alkylamines, mixtures of phosphoric acid and mono- and diisooctyl esters reacted with tert-alkylamines and primary (C12-14) amines, dodecanoic acid, triphenyl phosphorothionate and amine phosphates. Commercially available additives are, for example, the following products: IRGAMET® 39, IRGACOR® DSS G, Amin O; SARKOSYL® O (Ciba), COBRATEC® 122, CUVAN® 303, VANLUBE® 9123, CI-426, CI-426EP, CI-429 and CI-498.

The lubricant of the invention may additionally contain antiwear additives, antiwear additives and friction modifiers.

Antiwear additives are amines, amine phosphates, phosphates, thiophosphates, phosphorothionates, aryl phosphate, alkylated polysulfides, sulfurized amine compounds, sulfurized fatty acid methyl esters, naphthenic acids, nanoparticles from the groups of $Al_2O_3$, $SiO_2$, $TiO_2$, $ZrO_2$, $WO_3$, $Ta_2O_5$, $V_2O_5$, $CeO_2$, aluminum titanate, BN, $MoSi_2$, SiC, $Si_3N_4$, TiC, TiN, $ZrB_2$, clay minerals and/or mixtures thereof, and also thermally stable carbonates and/or sulfates, and mixtures of these components. The commercially available antiwear additives include IRGALUBE® TPPT, IRGALUBE® 232, IRGALUBE® 349, IRGALUBE® 211 and ADDITIN® RC3760 Liq 3960, FIRC-SHUN® FG 1505 and FG 1506, NA-LUBE® KR-015FG, LUBEBOND®, FLUORO® FG, SYNALOX® 40-D, ACHESON® FGA 1820 and ACHESON® FGA 1810.

The lubricant of the invention may contain pour point and viscosity improvers and adhesion additives. Pour point and viscosity improvers are selected from the groups of the linear and/or branched alkylated, acrylated and aliphatic polymers and copolymers, and polymerized fatty acid esters, for instance from the group of PIBs (polyisobutylenes) and PBs (polybutenes) in partly or fully hydrogenated form.

The lubricant of the invention may further contain UV stabilizers. UV stabilizers are selected from the groups of the nitrogen heterocycles, substituted nitrogen heterocycles, linear and branched alkylated, acylated, aliphatic nitrogen heterocycles, and derivatives thereof.

The lubricant of the invention may also contain solid lubricants. Solid lubricants are, for example, PTFE, BN, pyrophosphate, Zn oxide, Mg oxide, pyrophosphates, thiosulfates, Mg carbonate, Ca carbonate, Ca stearate, Zn sulfide, Mo sulfide, W sulfide, Sn sulfide, graphite, graphene, nanotubes, $SiO_2$ polymorphs or a mixture thereof.

The lubricant of the invention may contain emulsifiers. Emulsifiers are selected from the groups of the branched and/or linear ethoxylated and/or propoxylated alcohols and salts thereof, for example alcohols, C16-C18, ethoxylated, propoxylated, polyglycols, fatty acid esters, silicates, ionic surfactants, for example sodium salts of alkylsulfonic acids, where the chains contain C14-17 carbons.

The lubricant of the invention may contain defoamers. Defoamers are selected from the groups of the ethoxylated and/or propoxylated alcohols of chain lengths C10-C18, mono- and diglycerides of cooking fats, acrylates, propoxylated and/or ethoxylated alkyl ethers (polyglycols), alcohols, siloxanes.

A preferred form of the preparation method for an oil formulation is as follows: the vessel is initially charged with the ester compound of the general formula (I). The viscosity-imparting component and/or one or more further base oils are added, and a clear solution is produced with stirring and optionally heating to a defined temperature. Solid additives are then added at a temperature above their melting point and stirred until they have dissolved. Subsequently, the contents of the vessel are cooled down to not more than 60° C. and the liquid additives are added. After a further hour of stirring time, the oil can be dispensed.

In a preferred form of the preparation method for a grease formulation, the procedure is additionally as follows: the vessel is initially charged with the base oil mixture. The thickener components are added in a defined manner at a defined temperature while stirring. The grease thus formed is stirred for a defined period of time and, specifically in the case of use of soap-based thickeners, boiled until it is free of water. Solid additives are then added at a temperature above their melting point and stirred until they have dissolved. Subsequently, the contents of the vessel are cooled down to not more than 60° C. and the liquid additives are added. After a further hour of stirring time, the grease can be dispensed.

The lubricant compositions of the invention based on the ester compound of the general formulae (I), for example the ester compound of the general formulae (Ia) or (Ib) or (Ic), are used in the marine sector, in the inland waterways sector and in offshore facilities, i.e. for lubrication of chains, ball bearings, propeller rudders, propeller shafts, machine components and facilities that come into contact with saltwater in the marine sector or with water and aqueous media in inland waterways. Furthermore, they find use in the lubrication of machinery in the food processing industry, as hydraulic oil in the food processing industry, for transport and control chains, for apparatuses for the processing of cereal, flour and animal feed, and in baking ovens. They are also used for lubrication of roller bearings and slide bearings, transport and control chains in vehicle technology, in conveying technology, in mechanical engineering, in office technology and in industrial plants and machinery, and in the sectors of domestic appliances and consumer electronics. Furthermore, they are used for lubrication of bevel gears and spur gears of roller bearings in continuous casting plants and transport bearings in continuous kilns and for open crown gear lubrication in rotary kilns, tubular mills, drums and mixers, such as specifically in the cement, lime, gypsum, mining and chemical industries.

It should additionally be noted that the compounds of the invention, if they contain stereocenters, may either be racemic or enantiomerically enriched or enantiomerically pure compounds.

The section which follows elucidates the ester compounds of the invention and the preparation thereof, and also the use thereof in a lubricant composition, using corresponding experimental examples.

EXAMPLES

General Experimental Method 1 (GEM1): Biocatalytic Synthesis of Oleic Esters Proceeding From Oleic Acid and Guerbet Alcohols

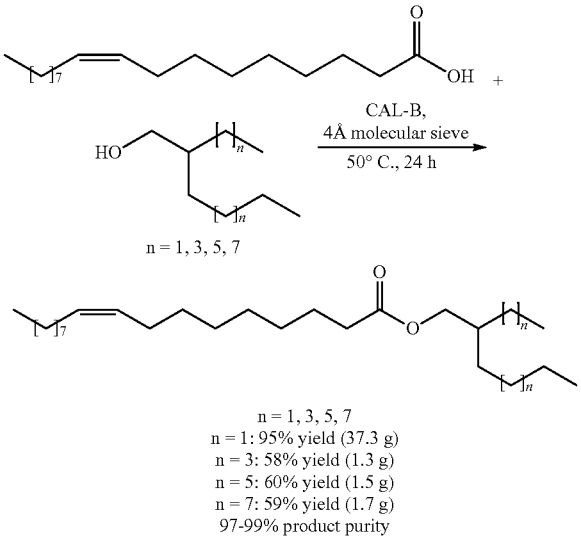

Scheme 2 Biocatalytic synthesis of oleic esters.

n = 1, 3, 5, 7
n = 1: 95% yield (37.3 g)
n = 3: 58% yield (1.3 g)
n = 5: 60% yield (1.5 g)
n = 7: 59% yield (1.7 g)
97-99% product purity To an initial charge of oleic acid (1.0 eq.) and Guerbet alcohol (1.0 eq.) were added CAL-B (Novozym 435, 30 mg/mmol substrate) and 4 Å molecular sieve (120 mg/mmol). The reaction mixture was stirred at 50° C. for 24 hours and then filtered through a 0.2 μM PTFE filter. The corresponding oleic ester was obtained in product purity 97-99%.

Example 1

Preparation of 2-ethylhexyl oleate proceeding from oleic acid and 2-ethylhexan-1-ol

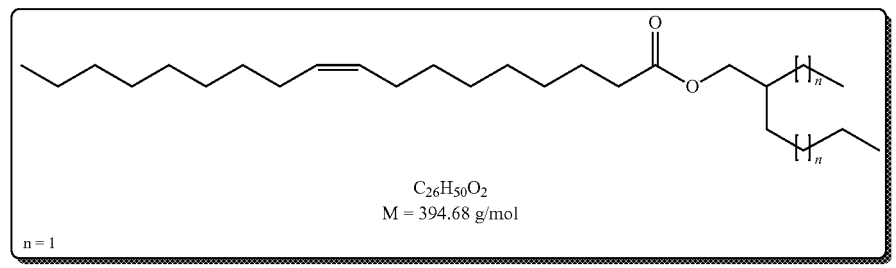

The synthesis was according to GEM 1. To oleic acid (31.6 ml, 100 mmol) and 2-ethylhexan-1-ol (15.6 ml, 100 mmol) were added Novozym 435 (3.0 g) and 4 Å molecular sieve (12.0 g). 2-Ethylhexyl oleate (99% purity) was obtained as a colorless liquid.

Yield: 37.3 g, 95%.

$^1$H NMR (500 MHz, CDCl$_3$): δ [ppm]=5.34 (m, 2H, CH=CH), 3.98 (dd, 2H, $^2$J=5.8 Hz, $^3$J=2.4 Hz, OCH$_2$), 2.29 (t, 2H, $^3$J=7.5 Hz, CH$_2$CH$_2$COOR), 2.01 (m, 4H, CH$_2$CH=CHCH$_2$), 1.61 (qi, 2H, $^3$J=7.3 Hz, CH$_2$CH$_2$COOR), 1.56 (sept, 1H, $^3$J=6.0 Hz, OCH$_2$CH), 1.28 (m, 28H), 0.88 (m, 9H, CH$_3$).

$^{13}$C NMR (125 MHz, CDCl$_3$): δ[ppm]=174.21, 130.11, 129.87, 66.76, 38.90, 34.58, 32.05, 30.57, 29.91, 29.84, 29.67, 29.47, 29.33, 29.29, 29.26, 29.07, 27.36, 27.31, 25.19, 23.95, 23.12, 22.83, 14.25, 14.18.

GC (FID): Phenomenex ZB-5MSi, 0.5 ml/min (H2), inj. temp.: 300° C., det. temp.: 350° C.; 300° C.→350° C. (5° C./min), 350° C. for 5 min, R$_f$=3.51 min.

HRMS (ESI): calculated for C$_{26}$H$_{50}$O$_2$Na [M+Na]$^+$: 417.3703, found: 417.3699.

IR (neat) [cm$^{-1}$]: 2956, 2922, 2853, 1736, 1461, 1240, 1171, 724.

Example 2

Preparation of 2-butyloctyl oleate proceeding from oleic acid and 2-butyloctan-1-ol The synthesis was according to GEM 1. To oleic acid (1.59 ml, 5.00 mmol) and 2-butyloctan-1-ol (1.12 ml, 5.00 mmol) were added Novozym 435 (150 mg) and 4 Å molecular sieve (600 mg). 2-Butyloctyl oleate (97% purity) was obtained as a colorless liquid.

Yield: 1.30 g, 58%.

$^1$H NMR (500 MHz, CDCl$_3$): δ [ppm]=5.34 (m, 2H, CH=CH), 3.96 (d, 2H, $^2$J=5.8 Hz, OCH$_2$), 2.29 (t, 2H, $^3$J=7.5 Hz, CH$_2$CH$_2$COOR), 2.01 (m, 4H, CH$_2$CH=CHCH$_2$), 1.61 (m, 2H, CH$_2$CH$_2$COOR), 1.60 (m, 1H, OCH$_2$CH), 1.28 (m, 36H), 0.88 (m, 9H, CH$_3$).

$^{13}$C NMR (125 MHz, CDCl$_3$): δ [ppm]=174.21, 130.11, 129.87, 67.16, 37.43, 34.60, 32.06, 31.97, 31.44, 31.11, 29.92, 29.86, 29.78, 29.68, 29.47, 29.35, 29.31, 29.28, 29.07, 27.36, 27.32, 26.82, 25.21, 23.14, 22.83, 22.81, 14.25, 14.24, 14.19.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_f$=4.27 min.

HRMS (ESI): calculated for C$_{30}$H$_{58}$O$_2$Na [M+Na]$^+$: 473.4329, found: 473.4324.

IR (neat) [cm$^{-1}$]: 2954, 2922, 2853, 1737, 1457, 1241, 1169, 723.

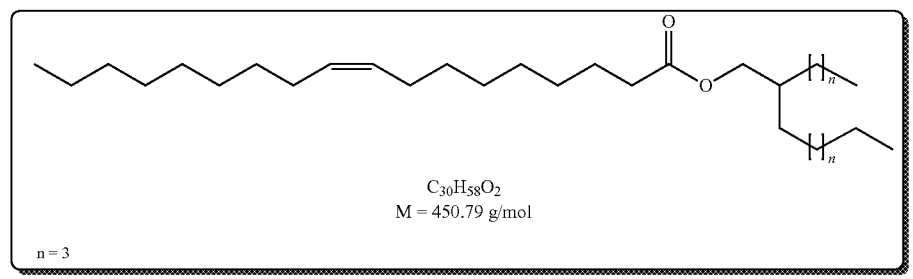

Example 3

Preparation of 2-hexyldecyl oleate proceeding from oleic acid and 2-hexyldecan-1-ol

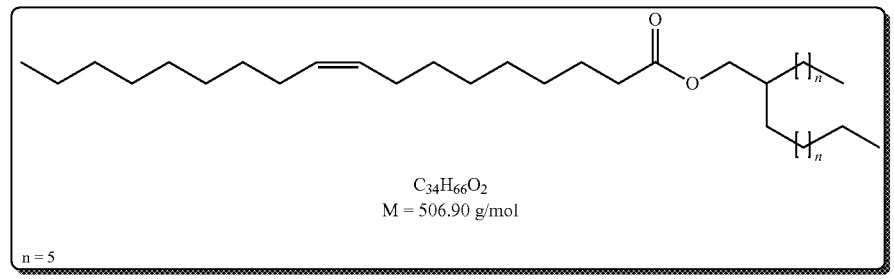

The synthesis was according to GEM 1. To oleic acid (1.59 ml, 5.00 mmol) and 2-hexyldecan-1-ol (1.44 ml, 5.00 mmol) were added Novozym 435 (150 mg) and 4 Å molecular sieve (600 mg). 2-Hexyldecyl oleate (97% purity) was obtained as a colorless liquid.

Yield: 1.51 g, 60%.

$^1$H NMR (500 MHz, CDCl$_3$): δ [ppm]=5.34 (m, 2H, CH=CH), 3.97 (d, 2H, $^2$J=5.8 Hz, OCH$_2$), 2.29 (t, 2H, $^3$J=7.5 Hz, CH$_2$CH$_2$COOR), 2.01 (m, 4H, CH$_2$CH=CHCH$_2$), 1.61 (m, 2H, CH$_2$CH$_2$COOR), 1.60 (m, 1H, OCH$_2$CH), 1.28 (m, 44H), 0.88 (m, 9H, CH$_3$).

$^{13}$C NMR (125 MHz, CDCl$_3$): δ [ppm]=174.22, 130.12, 129.87, 67.18, 37.45, 34.61, 32.06, 31.97, 31.44, 30.12, 29.92, 29.86, 29.78, 29.72, 29.68, 29.48, 29.36, 29.32, 29.29, 27.37, 27.32, 26.86, 26.82, 25.21, 22.84, 22.81, 14.26, 14.25.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_t$=5.65 min.

HRMS (ESI): calculated for C$_{34}$H$_{66}$O$_2$Na [M+Na]$^+$: 529.4955, found: 529.4951.

IR (neat) [cm$^{-1}$]: 2921, 2852, 1737, 1464, 1169, 722.

Example 4

Preparation of 2-octyldodecyl oleate proceeding from oleic acid and 2-octyldocecan-1-ol

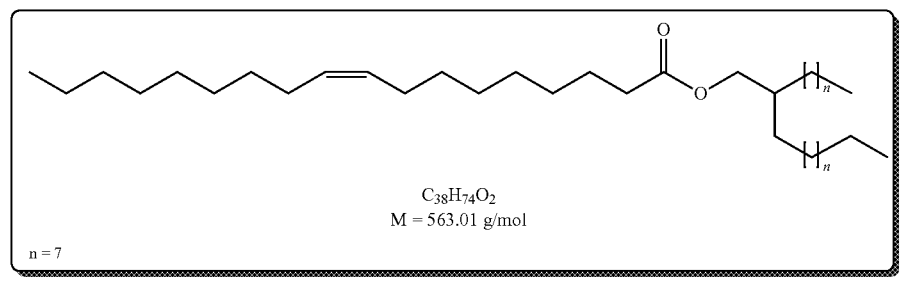

The synthesis was according to GEM 1. To oleic acid (1.59 ml, 5.00 mmol) and 2-octyldodecan-1-ol (1.78 ml, 5.00 mmol) were added Novozym 435 (150 mg) and 4 Å molecular sieve (600 mg). 2-Octyldodecyl oleate (98% purity) was obtained as a colorless liquid.

Yield: 1.67 g, 59%.

$^1$H NMR (500 MHz, CDCl$_3$): δ [ppm]=5.34 (m, 2H, CH=CH), 3.97 (d, 2H, $^2$J=5.8 Hz, OCH$_2$), 2.29 (t, 2H, $^3$J=7.5 Hz, CH$_2$CH$_2$COOR), 2.01 (m, 4H, CH$_2$CH=CHCH$_2$), 1.61 (m, 2H, CH$_2$CH$_2$COOR), 1.60 (m, 1H, OCH$_2$CH), 1.28 (m, 52H), 0.88 (m, 9H, CH$_3$).

$^{13}$C NMR (125 MHz, CDCl$_3$): δ [ppm]=174.22, 130.12, 129.87, 67.19, 37.43, 34.61, 32.08, 32.07, 31.42, 30.12, 29.92, 29.87, 29.82, 29.81, 29.77, 29.72, 29.69, 29.52, 29.48, 29.36, 29.32, 29.29, 27.37, 27.32, 26.85, 25.21, 22.84, 14.27.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_t$=7.70 min.

HRMS (ESI): calculated for C$_{34}$H$_{66}$O$_2$Na [M+Na]$^+$: 585.5581, found: 585.5568.

IR (neat) [cm$^{-1}$]: 2920, 2852, 1737, 1464, 1170, 722.

General Experimental Method 2 (GEM2): Ene Reaction of Oleic Acid/Ester with Paraformaldehyde and Lewis acids Scheme 3 Ene reaction of oleic acid/ester with paraformaldehyde.

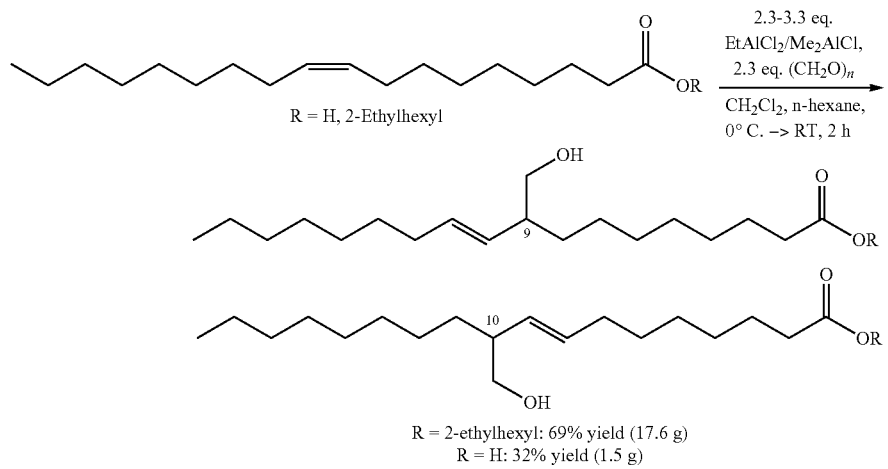

R = 2-ethylhexyl: 69% yield (17.6 g)
R = H: 32% yield (1.5 g)

In accordance with experimental methods of Metzger and Biermann (U. Biermann, J. Metzger, *Fat. Sci. Technol.* 1991, 93, 282-284; J. Metzger, U. Biermann, *Synthesis* 1992, 5, 463-465), an initial charge of oleic acid (1.0 eq.) or its 2-ethylhexyl ester (1.0 eq.) and paraformaldehyde (2.3 eq.) under argon in dry dichloromethane was cooled to 0° C. Subsequently, EtAlCl$_2$ or Me$_2$AlCl (2.3-3.3 eq., 1.0 M in n-hexane) was added dropwise and the reaction mixture was then warmed gradually to room temperature and stirred for two hours. Water (1:1 v/v) was added and the mixture was acidified to pH=1 with 4 M HCl. The phases were separated and the aqueous phase was extracted three times with diethyl ether (1:1 v/v). The combined extracts were dried over magnesium sulfate and freed of the solvent under reduced pressure. Subsequent column chromatography gave the products as colorless oils. The products were obtained as a 1:1 mixture of the C9 and C10 adducts.

Example 5

Preparation of a mixture of E-9-(hydroxymethyl) octadec-10-enoic acid and E-10-(hydroxymethyl) octadec-8-enoic acid The synthesis was according to GEM 2. Oleic acid (4.73 ml, 15 mmol) and paraformaldehyde (1.04 g, 34.5 mmol) were reacted with addition of Me$_2$AlCl (34.5 ml, 34.5 mmol). Workup and column chromatography (cyclohexane/ethyl acetate 7:3, v/v) gave the product as a colorless liquid.

Yield: 1.50 g, 32%.

$^1$H NMR (500 MHz, CDCl$_3$): δ [ppm]=5.52 (m, 1H, CH=CHCH), 5.13 (m, 1H, CH=CHCH), 3.52 (m, 1H, CH$_2$OH), 3.33 (m, 1H, CH$_2$OH), 2.34 (2 t, 2H, $^3$J=7.5 Hz, CH$_2$COO), 2.15 (m, 1H, CH=CHCH), 2.04 (m, 2H, CH$_2$CH=CH), 1.64 (m, 2H, CH$_2$CH$_2$COO), 1.27 (m, 22H), 0.88 (2 t, 3H, CH$_3$).

$^{13}$C NMR (125 MHz, CDCl$_3$): δ [ppm]=179.15, 179.07, 134.33, 133.88, 131.64, 131.30, 66.15, 66.10, 46.06, 34.01, 34.01, 32.82, 32.68, 32.03, 32.01, 31.27, 31.21, 29.82, 29.69, 29.68, 29.57, 29.45, 29.37, 29.29, 29.28, 29.26, 29.16, 28.99, 28.79, 27.24, 27.15, 27.07, 24.80, 24.75, 22.82, 22.81, 14.25.

The analytical data corresponded to the literature (J. Metzger, U. Biermann, *Synthesis* 1992, 5, 463-465).

Example 6

Preparation of a mixture of 2'-ethylhexyl E-9-(hydroxymethyl)octadec-10-enoate and 2'-ethylhexyl E-10-(hydroxymethyl)octadec-8-enoate

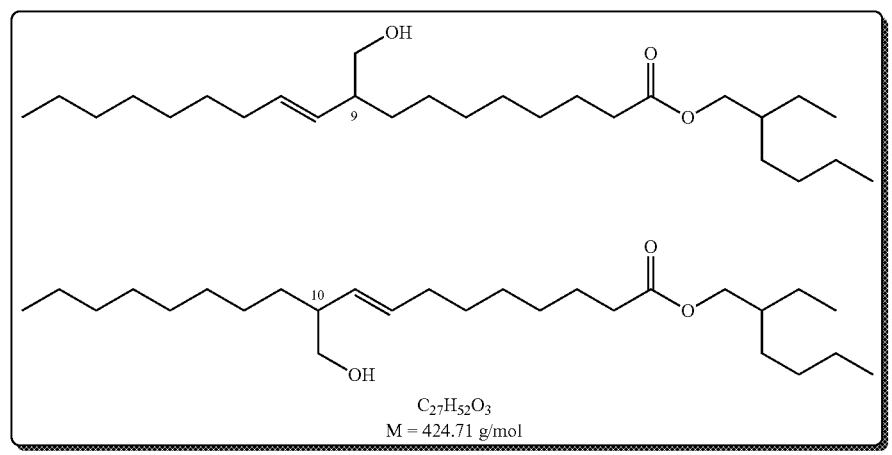

The synthesis was according to GEM 2. 2-Ethylhexyl oleate (23.7 g, 60 mmol) and paraformaldehyde (4.14 g, 138 mmol) were reacted with addition of EtAlCl$_2$ (198 ml, 198 mmol). Workup and vacuum distillation (at $10^{-3}$ mbar) gave the product as a colorless liquid.

Yield: 17.6 g, 69%.

$^1$H NMR (500 MHz, CDCl$_3$): δ [ppm]=5.51 (m, 1H, CH=CHCH), 5.12 (m, 1H, CH=CHCH), 3.98 (m, 2H, COOCH$_2$), 3.51 (m, 1H, CH$_2$OH) 3.32 (m, 1H, CH$_2$OH), 2.29 (2 t, 2H, $^3$J=7.5 Hz, CH$_2$COO), 2.12 (m, 1H, CH=CHCH), 2.02 (m, 2H, CH$_2$CH=CH), 1.61 (m, 2H, CH$_2$CH$_2$COO), 1.56 (m, 1H, OCH$_2$CH), 1.27 (m, 28H), 0.88 (3 t, 9H, CH$_3$).

$^{13}$C NMR (125 MHz, CDCl$_3$): δ [ppm]=174.21, 174.18, 134.27, 133.90, 131.58, 131.33, 66.79, 66.77, 66.12, 66.09, 46.09, 38.88, 34.56, 34.54, 32.81, 32.72, 32.02, 31.99, 31.25, 31.23, 30.56, 29.81, 29.67, 29.67, 29.64, 29.46, 29.44, 29.34, 29.28, 29.24, 29.10, 29.06, 28.90, 27.23, 27.18, 25.16, 25.12, 23.93, 23.12, 22.81, 22.80, 14.25, 14.24, 14.19, 11.13.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_f$=4.29, 4.53 min.

HRMS (ESI): calculated for C$_{27}$H$_{52}$O$_3$Na [M+Na]$^+$: 447.3809, found: 447.3813.

IR (neat) [cm$^{-1}$]: 2923, 2854, 1733, 1462, 1379, 1171, 1032, 969.

General experimental method 3 (GEM3): Palladium-catalyzed C=C hydrogenation of the unsaturated oleic acid derivatives Scheme 4 Palladium-catalyzed hydrogenation of the oleic acid derivatives.

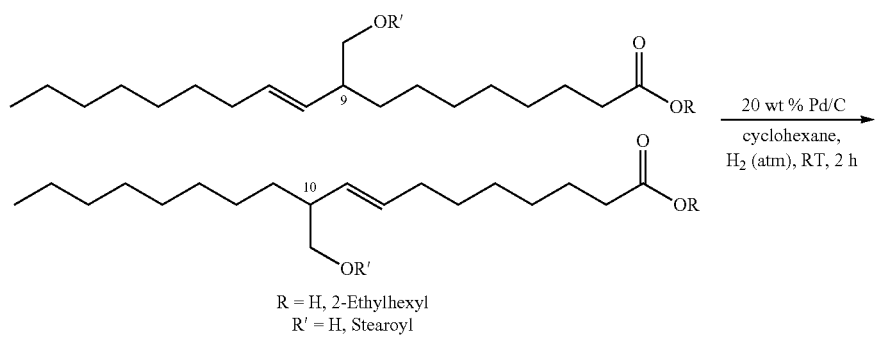

R = H, 2-Ethylhexyl
R' = H, Stearoyl

-continued

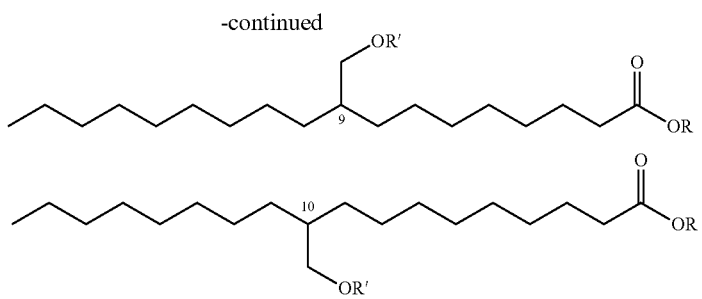

R = H, R' = H 25% yield (130 mg)
R = 2-ethylhexyl, R' = H 62% yield (660 mg)
R = 2-ethylhexyl, R' = Stearoyl 81% yield (1.62 g)

The unsaturated free acid (1.0 eq.) or the 2-ethylhexyl ester (1.0 eq.) was dissolved in cyclohexane under a hydrogen atmosphere and admixed with palladium on activated charcoal (Pd/C, 10% Pd, 20% by weight). The reaction mixture was stirred at room temperature for two hours and then filtered through a 0.2 µM PTFE filter. Column chromatography gave the desired product as a colorless oil.

Example 7

Preparation of a mixture of 9-(hydroxymethyl)octadecanoic acid and 10-(hydroxymethyl)octadecanoic acid

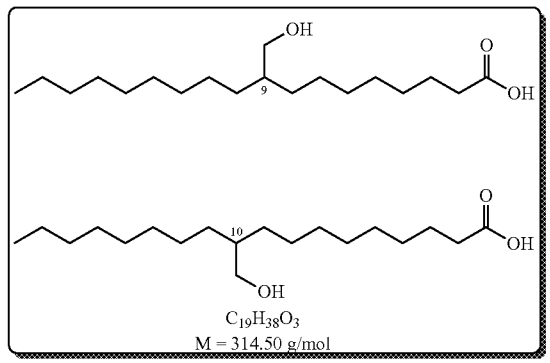

$C_{19}H_{38}O_3$
M = 314.50 g/mol

The synthesis was conducted according to GEM 3. A mixture of E-9-(hydroxymethyl)octadec-10-enoic acid and E-10-(hydroxymethyl)octadec-8-enoic acid (450 mg, 1.44 mmol) was dissolved under a hydrogen atmosphere in 25 ml of cyclohexane and admixed with Pd/C (90 mg). Workup and column chromatography (cyclohexane/ethyl acetate 1:2, v/v) gave the desired product as a colorless oil.

Yield: 130 mg, 25%.

$^1$H NMR (500 MHz, CDCl$_3$): δ [ppm]=3.53 (d, 2H, $^3$J=5.5 Hz CH$_2$OH), 2.35 (t, 2H, $^3$J=7.5 Hz, CH$_2$COO), 1.63 (qi, 2H, $^3$J=7.3 Hz, CH$_2$CH$_2$COO), 1.45 (m, 1H, HOCH$_2$CH), 1.27 (m, 36H), 0.88 (t, 3H, $^3$J=6.9 Hz, CH$_3$).

$^{13}$C NMR (125 MHz, CDCl$_3$): δ [ppm]=179.62, 65.81, 65.79, 40.59, 34.15, 34.14, 32.05, 31.07, 31.02, 30.99, 30.22, 30.05, 29.91, 29.80, 29.78, 29.76, 29.49, 29.30, 29.15, 29.13, 27.04, 26.92, 26.88, 24.80, 22.83, 14.27.

HRMS (ESI): calculated for $C_{19}H_{38}O_3$Na [M+Na]$^+$: 337.2713, found: 337.2717.

IR (neat) [cm$^{-1}$]: 2913, 2848, 1699, 1469, 1185, 972, 719.

Example 8

Preparation of a mixture of 2'-ethylhexyl 9-(hydroxymethyl)octadecanoate and 2'-ethylhexyl 10-(hydroxymethyl)octadecanoate

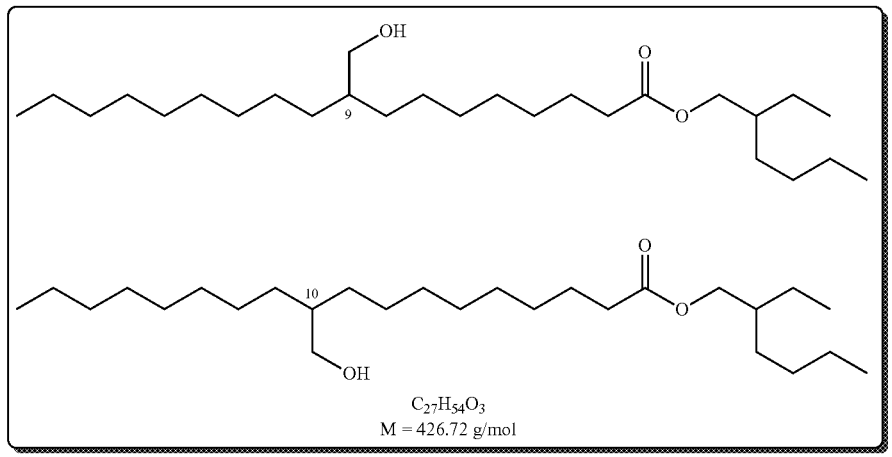

$C_{27}H_{54}O_3$
M = 426.72 g/mol

The synthesis was conducted according to GEM 3. A mixture of 2'-ethylhexyl E-9-(hydroxymethyl)octadec-10-enoate and 2'-ethylhexyl E-10-(hydroxymethyl)octadec-8-enoate (1.06 g, 2.50 mmol) was dissolved under a hydrogen atmosphere in 50 ml of cyclohexane and admixed with Pd/C (212 mg). Workup and column chromatography (cyclohexane/ethyl acetate 7:1, v/v) gave the desired product as a colorless oil.

Yield: 660 mg, 62%.

$^1$H NMR (500 MHz, CDCl$_3$): δ [ppm]=3.97 (m, 2H, COOCH$_2$), 3.54 (d, 2H, $^3$J=5.5 Hz CH$_2$OH), 2.29 (t, 2H, $^3$J=7.5 Hz, CH$_2$COO), 1.61 (m, 2H, CH$_2$CH$_2$COO), 1.56 (m, 1H, OCH$_2$CH), 1.27 (m, 36H), 0.89 (3 t, 9H, CH$_3$).

$^{13}$C NMR (125 MHz, CDCl$_3$): δ [ppm]=174.27, 174.26, 66.79, 65.85, 65.83, 40.67, 38.90, 34.60, 34.58, 32.05, 31.08, 31.07, 31.05, 30.57, 30.22, 30.14, 30.02, 29.81, 29.78, 29.76, 29.59, 29.49, 29.41, 29.40, 29.30, 29.07, 27.05, 27.01, 26.97, 25.19, 23.95, 23.13, 22.83, 14.27, 14.20, 11.15.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_t$=4.61 min.

HRMS (ESI): calculated for C$_{27}$H$_{54}$O$_3$Na [M+Na]$^+$: 449.3965, found: 449.3975.

IR (neat) [cm$^{-1}$]: 2921, 2853, 1736, 1459, 1171, 1031.

Example 9

Preparation of a mixture of 2'-ethylhexyl 9-((stearoyloxy)methyl)octadecanoate and 2'-ethylhexyl 10-((stearoyloxy)methyl)octadecanoate The synthesis was conducted according to GEM 3. A mixture of 2'-ethylhexyl E-9-(hydroxymethyl)octadec-10-enoate and 2'-ethylhexyl E-10-(hydroxymethyl)octadec-8-enoate (2.00 g, 2.90 mmol) was dissolved under a hydrogen atmosphere in 50 ml of cyclohexane and admixed with Pd/C (400 mg). Workup and column chromatography (cyclohexane/ethyl acetate 15:1, v/v) gave the desired product as a colorless oil.

Yield: 1.62 g, 81%.

$^1$H NMR (500 MHz, CDCl$_3$): δ [ppm]=3.97 (m, 4H, COOCH$_2$), 2.28 (t, 4H, $^3$J=7.5 Hz, CH$_2$COO), 1.61 (m, 6H, CH$_2$CH$_2$COO), 1.25 (m, 62H), 0.89 (m, 12H, CH$_3$).

$^{13}$C NMR (125 MHz, CDCl$_3$): δ [ppm]=174.22, 174.16, 67.13, 66.75, 38.91, 37.46, 34.60, 34.58, 32.07, 31.42, 30.58, 30.12, 30.06, 29.94, 29.85, 29.81, 29.76, 29.71, 29.65, 29.63, 29.58, 29.46, 29.43, 29.39, 29.34, 29.32, 29.07, 26.85, 25.21, 23.95, 23.12, 22.84, 14.25, 14.18, 11.13.

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_t$=14.4 min.

HRMS (ESI): calculated for C$_{45}$H$_{88}$O$_4$Na [M+Na]$^+$: 715.6575, found: 715.6573.

IR (neat) [cm$^{-1}$]: 2921, 2852, 1736, 1463, 1169.

TABLE 1

Chemical and physical properties of the product prepared by example 9

| Parameter | Method | Unit | Product prepared by example 9 | |
|---|---|---|---|---|
| Appearance | | | liquid clear colorless | |
| Kin. vis. 40° C. | ASTM | mm$^2$/s | 29.8 | |
| Kin. vis. 100° C. | D 7042 | | 6.56 | |
| VI | | | 184.1 | |
| Biodegradability | OECD | % | 81.3 | 301 F. |

General Experimental Method 4 (GEM4): Biocatalytic Esterification of Fatty Acids with Hydroxymethylated Stearic Acid Derivatives to Give "Dimers"

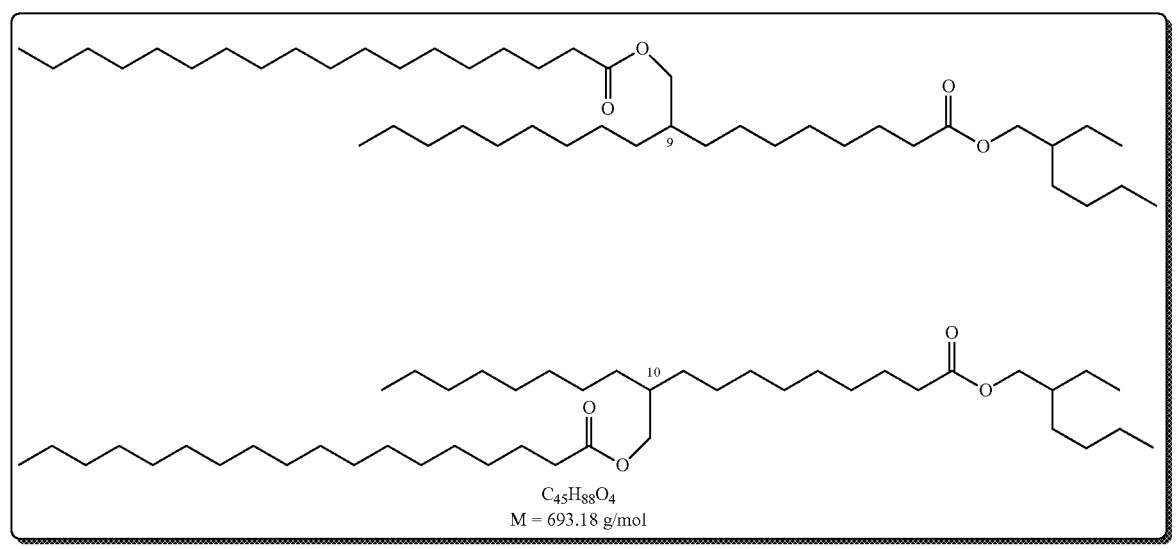

Scheme 5 Biocatalytic "dimer" synthesis.

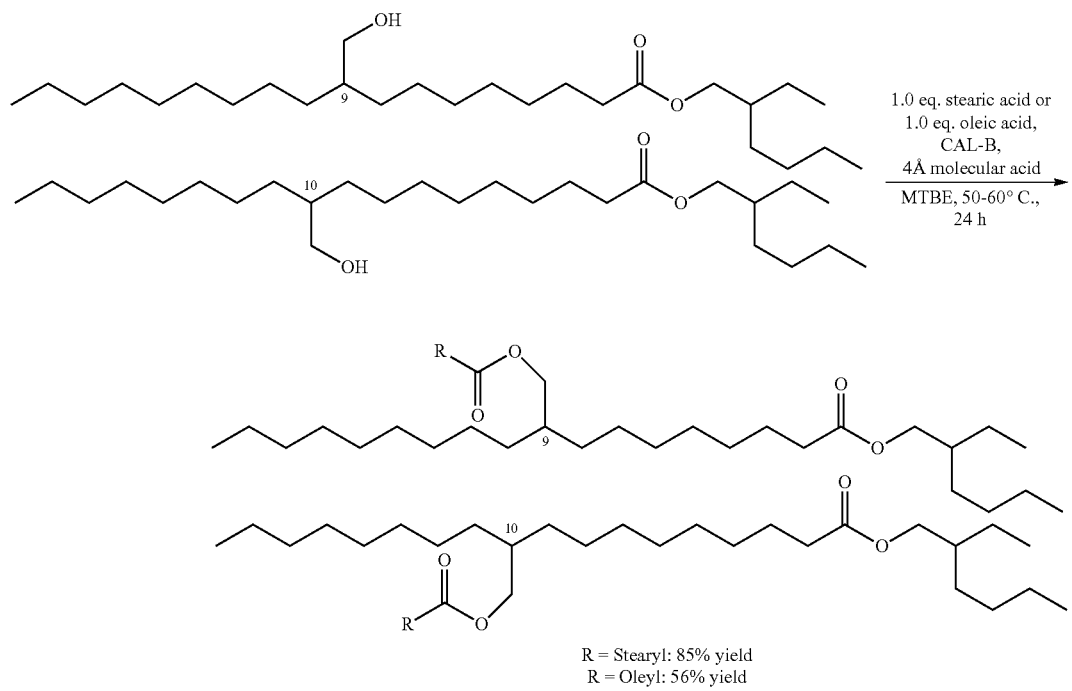

The hydroxymethylated 2'-ethylhexyl stearate (1.0 eq.) was dissolved in MTBE and admixed with Novozym 435 (CAL-B, 30 mg/mmol) and 4 Å molecular sieve (120 mg/mmol) and a fatty acid (1.0 eq.). The reaction mixture was stirred at 50 to 60° C. for 24 hours and then filtered through a 0.2 µM PTFE filter. Removing the solvent under reduced pressure gave the product as a colorless oil.

Example 10

Preparation of a mixture of 2'-ethylhexyl 9-((stearoyloxy)methyl)octadecanoate and 2'-ethylhexyl 10-((stearoyloxy)methyl)octadecanoate

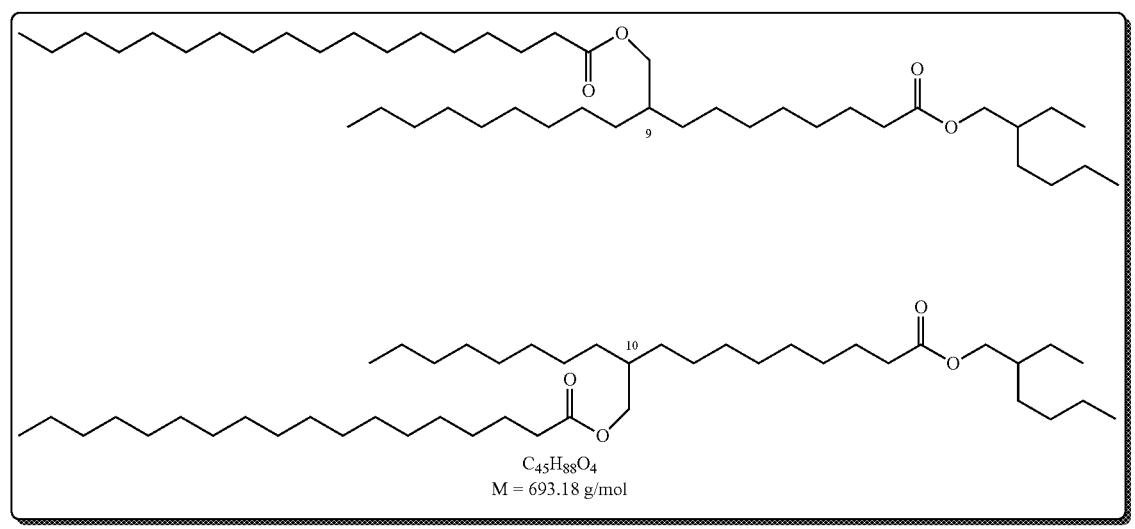

The synthesis was according to GEM 4. A mixture of 2'-ethylhexyl 9- and 2'-ethylhexyl 10-(hydroxymethyl)octadecanoate (51.7 mg, 100 μmol) and stearic acid (28.4 mg, 100 μmol) were dissolved in 50 μl of MTBE and admixed with Novozym 435 (3 mg) and 4 Å molecular sieve (12 mg) and stirred at 50° C. Workup gave the desired product as a colorless oil.

Yield: 58 mg, 85%.

$^1$H NMR (500 MHz, CDCl$_3$): δ [ppm]=3.98 (m, 2H, COOCH$_2$), 3.95 (m, 2H, COOCH$_2$), 2.29 (2 t, 4H, $^3$J=7.4 Hz, CH$_2$COO), 1.61 (m, 4H, CH$_2$CH$_2$COO), 1.56 (m, 2H, OCH$_2$CH), 1.27 (m, 62H), 0.89 (4 t, 12H, CH$_3$).

$^{13}$C NMR (125 MHz, CDCl$_3$): δ [ppm]=174.29, 174.27, 174.22, 67.16, 66.78, 38.91, 37.46, 34.63, 34.60, 34.59, 32.08, 32.07, 31.43, 30.58, 30.13, 29.86, 29.83, 29.82, 29.77, 29.72, 29.66, 29.64, 29.52, 29.51, 29.48, 29.44, 29.35, 29.33, 29.08, 26.86, 25.22, 25.21, 23.96, 23.14, 22.85, 14.28, 14.21, 11.15.

The analytical data correspond to those of the compound of example 9.

Example 11

Preparation of a mixture of 2'-ethylhexyl 9-((stearoyloxy)methyl)octadec-10-enoate and 2'-ethylhexyl 10-((stearoyloxy)methyl)octadec-8-enoate A mixture of 2'-ethylhexyl E-9-(hydroxymethyl)octadec-10-enoate and 2'-ethylhexyl E-10-(hydroxymethyl)octadec-8-enoate (10.0 g, 23.5 mmol) was mixed with stearic acid (6.70 g, 23.5 mmol) and heated to 70° C., which melted the stearic acid. Novozym 435 (CAL-B, 706 mg, 30 mg/mmol) and 4 Å molecular sieve (3.3 g, 120 mg/mmol) were added. The reaction mixture was stirred at 70° C. for 24 hours. Subsequently, it was filtered through a 0.2 μM PTFE filter.

Removing the solvent in vacuo and filtration through silica gel (cyclohexane/ethyl acetate 15:1, v/v) gave the product as a colorless oil.

Yield: 11.9 g, 73%.

$^1$H NMR (500 MHz, CDCl$_3$): δ [ppm]=5.40 (m, 1H, CH=CH), 5.14 (m, 1H, CH=CH), 3.98 (m, 2H, COOCH$_2$), 2.29 (m, 4H, CH$_2$COO), 1.97 (m, 2H, CHCH$_2$) 1.61 (m, 5H, CH$_2$CH$_2$COO+OCH$_2$CH), 1.27 (m, 60H), 0.88 (4 t, 12H, CH$_3$).

GC (FID): Phenomenex ZB-5MSi, 0.5 ml/min (H2), inj. temp.: 300° C., det. temp.: 350° C.; 300° C.→350° C. (5° C./min), 350° C. for 5 min; R$_t$=14.1 min.

HRMS (ESI): calculated for C$_{45}$H$_{86}$O$_4$Na [M+Na]$^+$: 713, 6418, found: 713,6419.

IR (neat) [cm$^{-1}$]: 2959, 2926, 2856, 1736, 1257, 1011, 865, 790, 700.

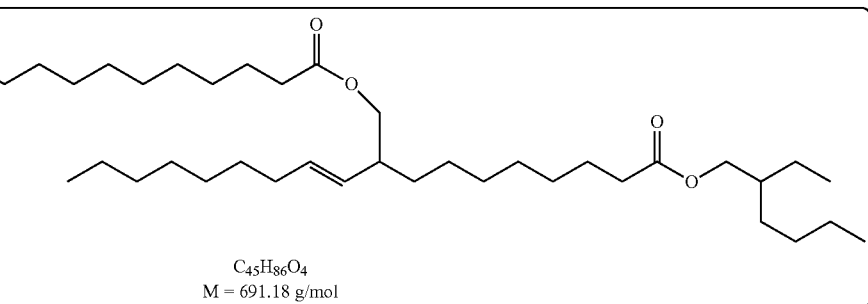

C$_{45}$H$_{86}$O$_4$
M = 691.18 g/mol

Example 12

Preparation of a mixture of 2'-ethylhexyl 9-((octadec-9-enoyloxy)methyl)octadecanoate and 2'-ethylhexyl 10-((octadec-9-enoyloxy)methyl)octadecanoate

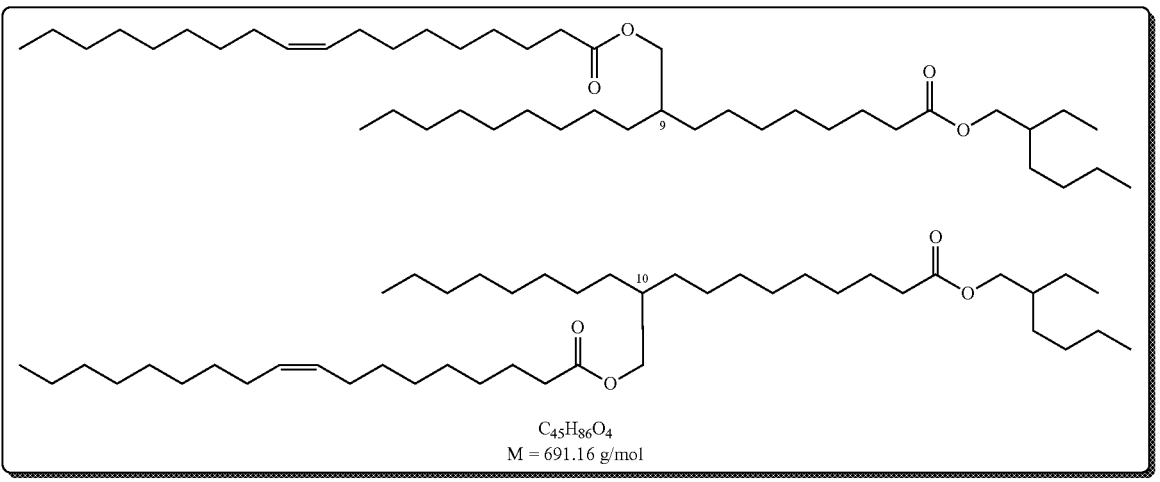

$C_{45}H_{86}O_4$
M = 691.16 g/mol

The synthesis was according to GEM 4. A mixture of 2'-ethylhexyl 9-(hydroxymethyl)octadecanoate and 2"-ethylhexyl 10-(hydroxymethyl)octadecanoate (51.7 mg, 100 µmol) and oleic acid (28.2 mg, 100 µmol) were admixed with Novozym 435 (3 mg) and 4 Å molecular sieve (12 mg) and stirred at 60° C. Workup gave the desired product as a colorless oil.

Yield: 39 mg, 56%.

$^1$H NMR (500 MHz, CDCl$_3$): δ [ppm]=5.34 (m, 2H, CH=CH), 3.98 (m, 2H, COOCH$_2$), 3.95 (m, 2H, COOCH$_2$), 2.29 (2 t, 4H, $^3$J=7.4 Hz, CH$_2$COO), 1.61 (m, 4H, CH$_2$CH$_2$COO), 1.56 (m, 2H, OCH$_2$CH), 1.27 (m, 58H), 0.89 (4 t, 12H, CH$_3$).

MS (ESI): m/z=691.5 [M+H]$^+$.

IR (neat) [cm$^{-1}$]: 2959, 2926, 2856, 1736, 1257, 1011, 865, 790, 700.

Example 13

Preparation of a mixture of 2'-ethylhexyl 9-(((12-hydroxyoctadecanoyl)-oxy)methyl)octadecanoate and 2'-ethylhexyl 10-(((12-hydroxyoctadecanoyl)-oxy)methyl)octadecanoate

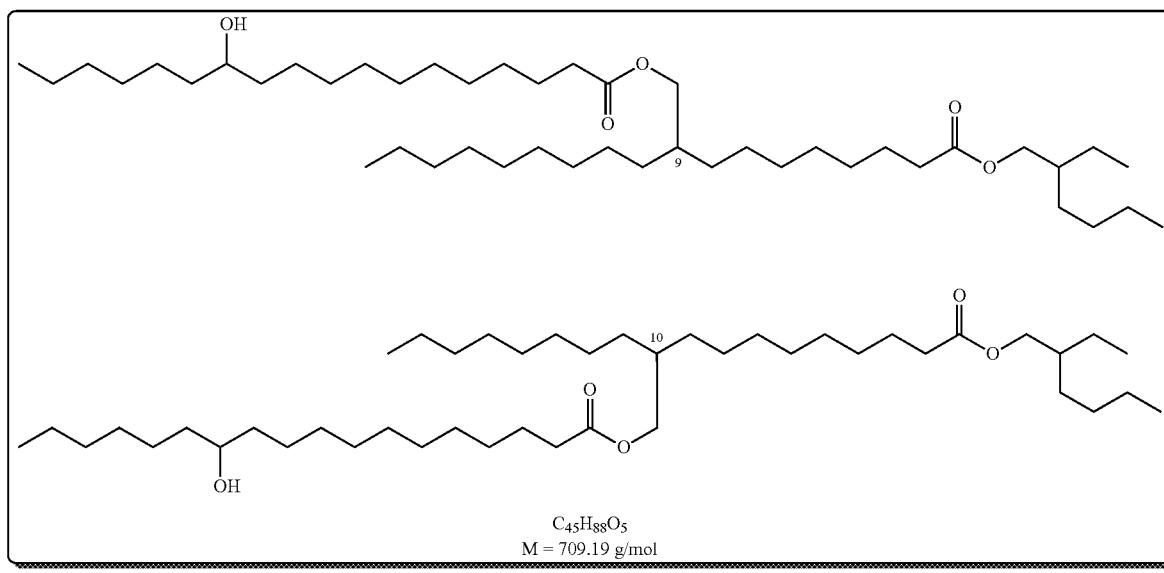

$C_{45}H_{88}O_5$
M = 709.19 g/mol

The synthesis was according to GEM 4. A mixture of 2'-ethylhexyl 9-(hydroxymethyl)octadecanoate and 2'-ethylhexyl 10-(hydroxymethyl)octadecanoate (213.2 mg; 500 µmol), and 12-hydroxystearic acid (142.8 mg; 480 µmol) were stirred with 4 Å molecular sieve (59.53 mg), Novozym 435 (14.5 mg) and MTBE (0.5 ml) at 50° C. for 24 h. Workup gave the desired product as a colorless oil.

Yield: 267 mg, 76%.

$^1$H NMR (500 MHz, CDCl$_3$): δ [ppm]=4.05-3,86 (m, 4H, COOCH$_2$); 3.58 (dt, 1H, $^3$J=7.4, 4.2 Hz, CH$_2$OH); 2.29 (t, 4H, $^3$J=7.5 Hz, CH$_2$COO); 1.58 (dt, 6H, $^3$J=24,3, 6,6 Hz); 1.41 (d, 6H, $^3$J=6.5 Hz); 1,37-1,20 (m, 55H); 0.88 (td, 12H, $^3$J=6.9, 6.3, 3.8 Hz, CH$_3$).

$^{13}$C NMR (125 MHz, CDCl$_3$): δ [ppm]=174.22, 150.97, 67.14, 66.78, 38.91, 37.63, 37.46, 34.59, 32.05, 31.99, 31.43, 30.58, 30.11, 29.85, 29.83, 29.75, 29.73, 29.69, 29.66, 29.61, 29.58, 29.52, 29.49, 29.46, 29.43, 29.40, 29.32, 29.30, 29.07, 26.84, 25.79, 25.76, 25.19, 23.95, 23.12, 22.82, 22.76, 14.24, 14.22, 14.18, 11.13.

HRMS (ESI): calculated for C$_{45}$H$_{88}$O$_5$Na$^+$: 731.6524; found: 731.6521.

Example 14

Preparation of a mixture of (E)-11-((2-ethylhexyl)oxy)-2-octyl-11-oxoundec-3-en-1-yl ((E)-2-(8-((2-ethylhexyl)oxy)-8-oxooctyl)undec-3-en-1-yl)adipate, bis((E)-11-((2-ethylhexyl)oxy)-2-octyl-11-oxoundec-3-en-1-yl) adipate and bis((E)-2-(8-((2-ethylhexyl)oxy)-8-oxooctyl)undec-3-en-1-yl)adipate The synthesis was in accordance with GEM 4. To a mixture of 2'-ethylhexyl E-9-(hydroxymethyl)octadec-10-enoate and 2'-ethyl hexyl E-10-(hydroxymethyl)octadec-8-enoate (999.6 mg, 2.4 mmol) and adipic acid (172.6 mg, 1.2 mmol) were added Novozym 435 (70.6 mg) and 4 Å molecular sieve (288 mg), and the mixture was stirred at 60° C. Workup gave the desired product as a yellowish oil.

Yield: 1.06 g, 94%.

$^1$H NMR (500 MHz, CDCl$_3$): δ [ppm]=5.43 (m, 2H, CH=CH), 5.19-5.09 (m, 2H, CH=CH), 4.07-3.86 (m, 8H, COOCH$_2$), 2.29 (m, 8H, CH$_2$COO), 1.98 (m, 4H, CHCH$_2$) 1.61 (m, 10H, CH$_2$CH$_2$COO+OCH$_2$CH), 1.27 (m, 60H), 0.88 (4 t, 16H, CH$_3$)

$^{13}$C NMR (125 MHz, CDCl$_3$): δ [ppm]=174.13, 174.06, 174.02, 173.53, 173.51, 173.32, 132.68, 132.62, 132.38, 132.32, 130.56, 130.44, 130.38, 67.73, 67.59, 66.80, 66.64, 42.10, 42.05, 38.76, 38.74, 34.47, 34.43, 34.39, 34.01, 33.96, 32.61, 32.57, 32.55, 31.93, 31.89, 31.46, 30.43, 30.41, 29.70, 29.65, 29.54, 29.50, 29.37, 29.32, 29.31, 29.25, 29.18, 29.17, 29.06, 29.02, 28.93, 28.80, 28.76, 26.88, 25.07, 25.04, 25.01, 24.48, 24.45, 23.81, 23.79, 22.99, 22.97, 22.70, 22.68, 14.12, 14.06, 11.00, 10.99.

HRMS (ESI): calculated for C$_{60}$H$_{110}$O$_8$Na$^+$: 981.8093; found: 981.8094.

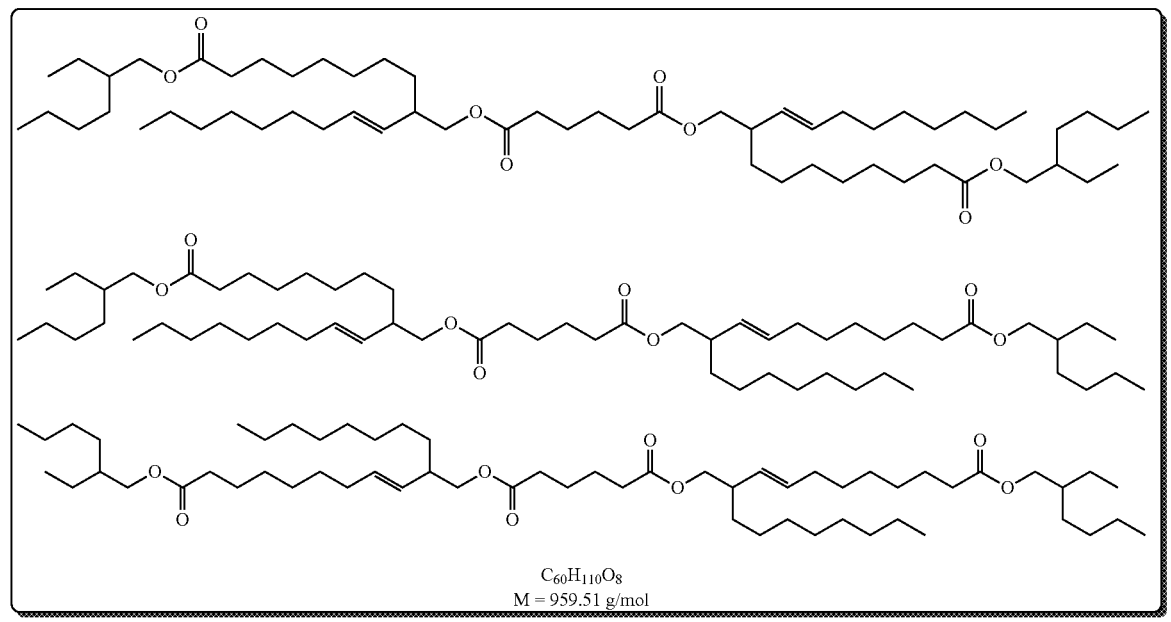

C$_{60}$H$_{110}$O$_8$
M = 959.51 g/mol

Example 15

Preparation of (Z)-hexane-1,6-diyldioleate

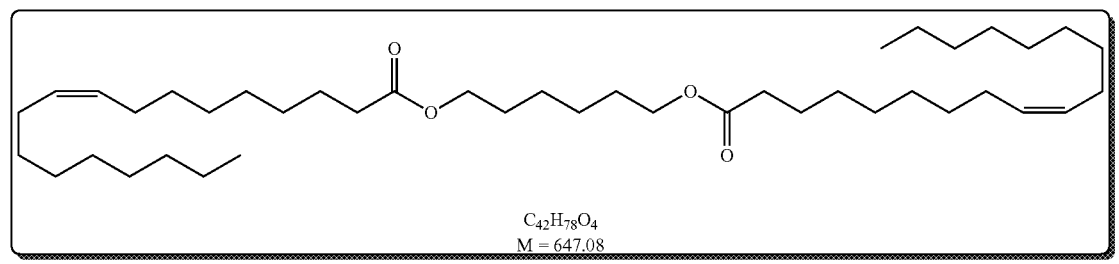

The synthesis was in accordance with experimental methods of Raghunanan et al. (L. Raghunanan, S. Narine *ACS Sust. Chem. & Eng.* 2016 4 (3), 693-700) and Neises et al. (B. Neises, W. Steglich, *Angew. Chem. Int. Ed. Engl.* 1978, 17, 522-524). Oleic acid (5.01 g, 17.7 mmol), hexane-1,6-diol (804.6 mg, 6.8 mmol), N,N-dimethylaminopyridine (86.7 mg, 0.71 mmol) and N,N'-dicyclohexylcarbodiimide (2.84 g, 13.8 mmol) were stirred in dichloromethane at room temperature. After 18 h, the phases were separated and the aqueous phase was extracted three times with dichloromethane (1:1 v/v). The combined extracts were dried over magnesium sulfate and freed of the solvent under reduced pressure. The product was obtained as a yellowish oil.

Yield: 2.79 g, 63%.

$^1$H NMR (500 MHz, CDCl$_3$): δ [ppm]=5.34 (4H, m, CH=CH), 4.06 (4H, t, O—CH$_2$), 2.28 (4H, t, CH$_2$COO), 2.00 (8H, m, CH=CH—CH$_2$), 1.63 (8H, m, O—CH$_2$—CH$_2$, CH$_2$—CH$_2$—COO), 1.21-1.35 (44H, m), 0.88 (6H, t, CH$_3$).

MS (ESI): m/z=669.6 [M+Na]$^+$.

The analytical data correspond to the literature (L. Raghunanan, S. Narine *ACS Sust. Chem. & Eng.* 2016 4 (3), 693-700).

Example 16

Preparation of a mixture of 6-(((E)-9-(hydroxymethyl)octadec-10-enoyl)oxy)hexyl (E)-10-(hydroxymethyl)octadec-8-enoate, hexane-1,6-diyl (10E,10'E)-bis(9-(hydroxymethyl)octadec-10-enoate) and hexane-1,6-diyl (8E,8'E)-bis(10-(hydroxymethyl)octadec-8-enoate)

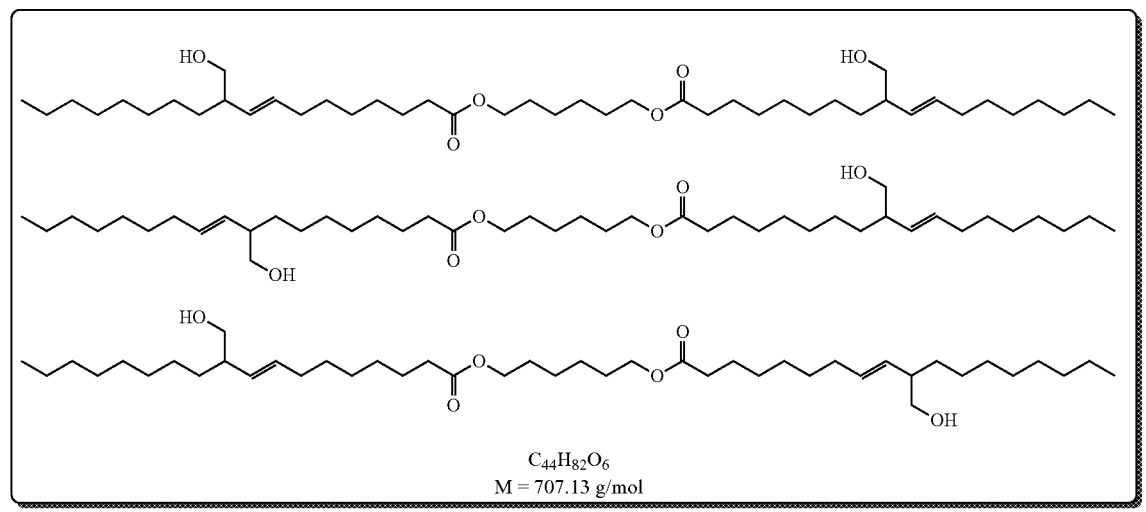

The synthesis was according to GEM 2. (Z)-Hexane-1,6-diyl dioleate (1.73 g, 2.68 mmol) and paraformaldehyde (373 mg, 12.4 mmol) were converted with addition of EtAlCl$_2$ (19 ml, 19 mmol). Workup and column chromatography (cyclohexane/ethyl acetate 15:1, v/v) gave the desired product as a colorless oil.

Yield: 353 mg, 19%.

$^1$H NMR (500 MHz, CDCl$_3$): δ [ppm]=5.51 (m, 2H, CH=CHCH), 5.13 (m, 2H, CH=CHCH), 4.06 (m, 4H, COOCH$_2$), 3.53 (m, 2H, CH$_2$OH) 3.32 (m, 2H, CH$_2$OH), 2.29 (t, 4H, CH$_2$COO), 2.14 (m, 2H, CH=CHCH), 2.02 (m, 4H, CH$_2$CH=CH), 1.63 (m, 8H, CH$_2$CH$_2$COO, OCH$_2$CH), 1.32 (m, 42H), 0.88 (t, 6H, CH$_3$).

$^{13}$C NMR (125 MHz, CDCl$_3$): δ [ppm]=134.29, 133.92, 131.62, 131.34, 66.13, 64.32, 46.10, 34.50, 34.48, 32.83, 32.73, 32.04, 32.01, 31.28, 31.24, 29.82, 29.69, 29.64, 29.46, 29.34, 29.29, 29.26, 29.11, 28.91, 28.71, 27.25, 27.19, 25.78, 25.13, 25.09, 22.81, 14.26.

HRMS (ESI): calculated for C$_{44}$H$_{82}$O$_6$Na$^+$: 729,6004; found: 729,6014.

General Experimental Method 5 (GEM5): Preparation of Higher Molecular Weight Fatty Acid Esters Using the Acid Chlorides The acid chlorides were purchased commercially or prepared by the following method: thionyl chloride (15 eq.) was slowly added dropwise at 0° C. while stirring to the carboxylic acid (1.0 eq.) dissolved in toluene. After heating under reflux for 16 h, the excess thionyl chloride and the solvent was removed by means of microdistillation in order to obtain the acid chloride. This was used immediately.

The fatty acid component with a free alcohol function (1.0 eq.) in toluene was initially charged together with pyridine (1.1 eq.) and, while stirring and cooling with ice, the acid chloride (1.2 eq.) was added gradually. The mixture was brought to room temperature within 15 min and then heated under reflux for 6-16 h. After phase separation, the aqueous phase was acidified with acetic acid and extracted twice more with ethyl acetate. The combined extracts were dried over magnesium sulfate and concentrated to dryness under reduced pressure. Column chromatography gave the desired products.

Scheme 6 Ester synthesis of higher homologs with the aid of acid chlorides.

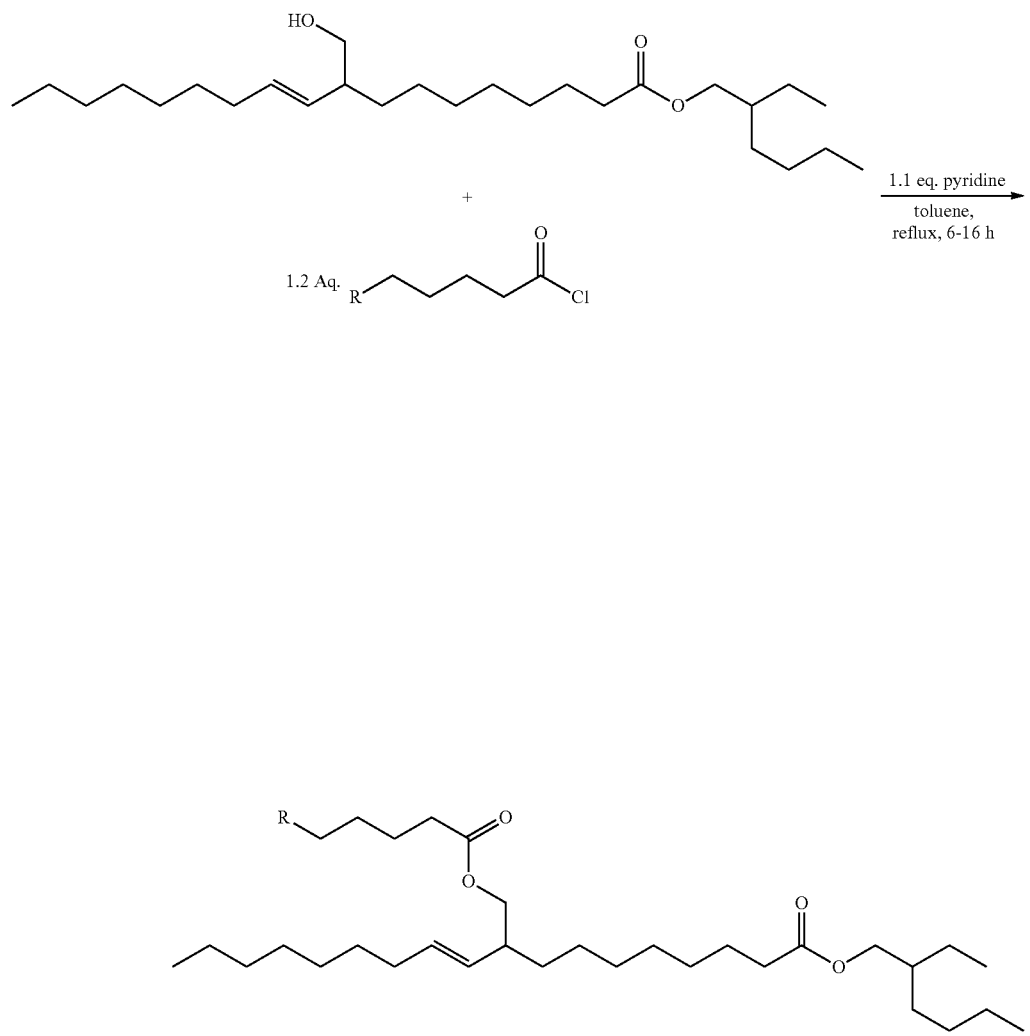

Example 17

Preparation of a mixture of 2'-ethylhexyl 9-(((12-(hexanoyloxy)octadecanoyl)-oxy)methyl)octadecanoate and 2'-ethylhexyl 10-(((12-(hexanoyloxy)-octadecanoyl)oxy)methyl)octadecanoate

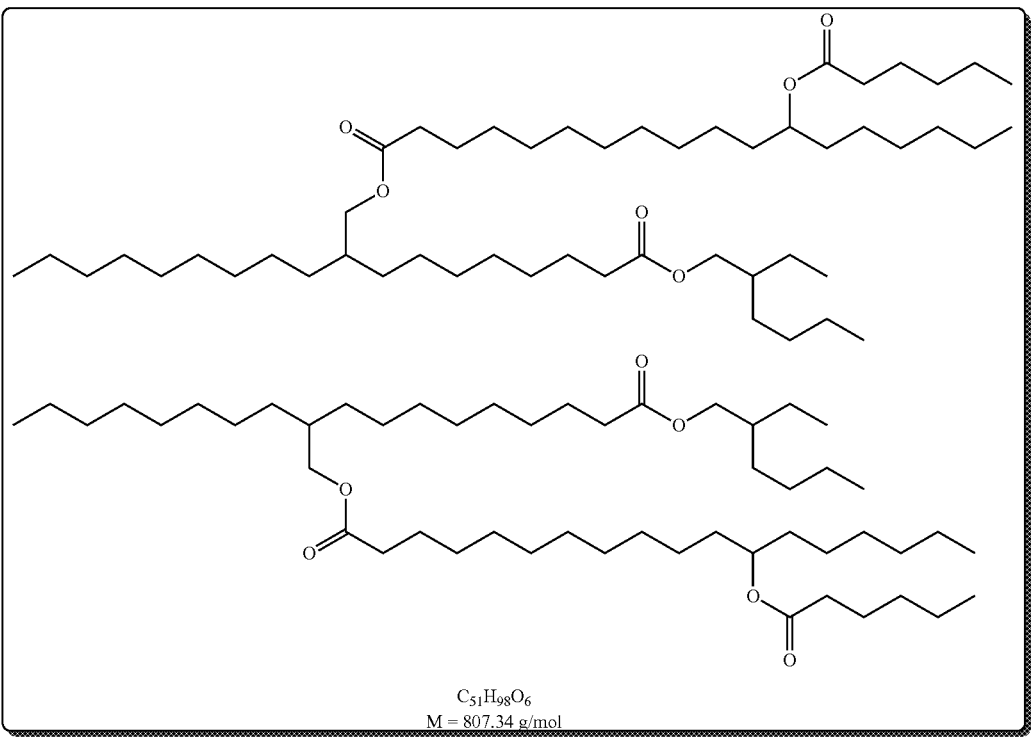

$C_{51}H_{98}O_6$
M = 807.34 g/mol

The synthesis was according to GEM 5. A mixture of 2'-ethylhexyl 9-(((12-hydroxyoctadecanoyl)oxy)methyl)octadecanoate and 2'-ethylhexyl 10-(((12-hydroxyoctadecanoyl)oxy)methyl)octadecanoate (2.04 g, 2.87 mmol) was reacted with pyridine (0.25 ml, 3.16 mmol) and hexanoyl chloride (0.5 ml, 3.58 mmol). Workup and column chromatography using a C18-RP column (acetonitrile) gave the desired product as a colorless oil.

Yield: 8 mg, 2%. 4.86 (s, 1H), 4.01-3.91 (m, 8H), 2.27 (s, 5H), 1.76-1.15 (m, 64H), 0.89 (s, 9H).

$^1$H NMR (500 MHz, CDCl$_3$): δ [ppm]=4,86 (m, 1H, COOCH), 4.01-3.91 (m, 4H, COOCH$_2$); 2.27 (m, 6H, CH$_2$COO); 1.76-1.15 (m, 72H); 0.88 (m, 15H, CH$_3$).

HRMS (ESI): calculated for $C_{51}H_{98}O_6Na^+$: 829.7256; found: 829.7261.

Example 18

Preparation of a mixture 6-(((E)-9-((stearoyloxy)methyl)octadec-10-enoyl)oxy)hexyl (E)-10-((stearoyloxy)methyl)octadec-8-enoate, hexane-1,6-diyl (10E,10'E)-bis(9-((stearoyloxy)methyl)octadec-10-enoate) and hexane-1,6-diyl (8E,8'E)-bis(10-((stearoyloxy)methyl)octadec-8-enoate)

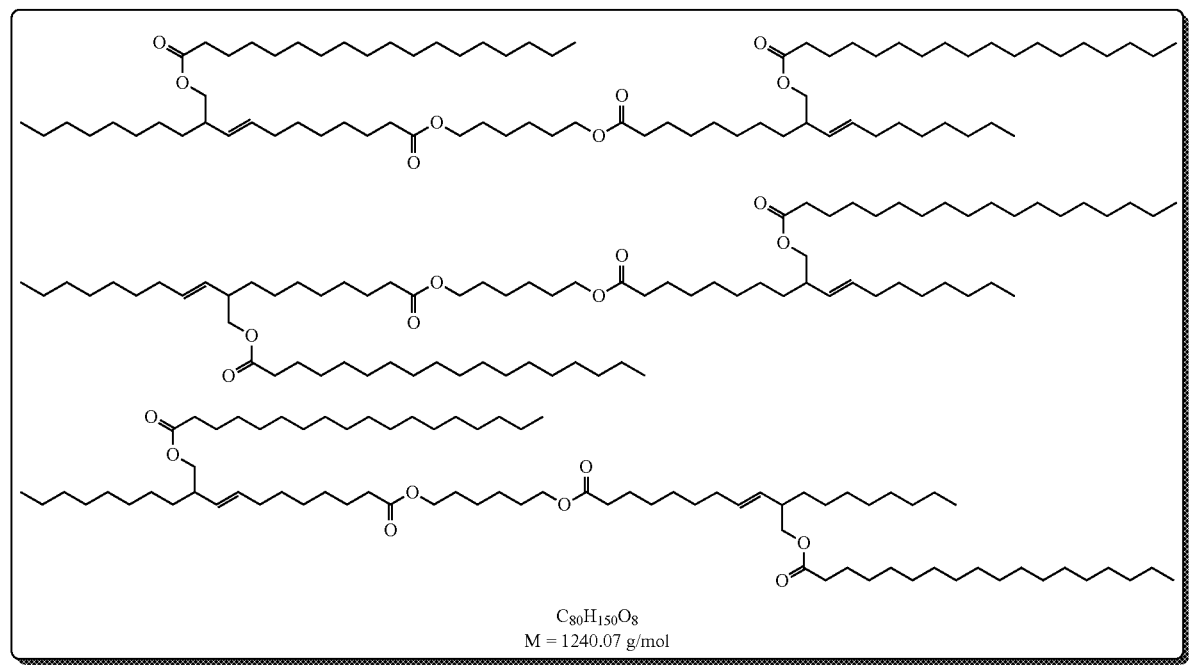

$C_{80}H_{150}O_8$
M = 1240.07 g/mol

The synthesis was according to GEM 5. A mixture of 6-(((E)-9-(hydroxymethyl)octadec-10-enoyl)oxy)hexyl (E)-10-(hydroxymethyl)octadec-8-enoate, hexane-1,6-diyl (10E,10'E)-bis(9-(hydroxymethyl)octadec-10-enoate) and hexane-1,6-diyl (8E,8'E)-bis(10-(hydroxymethyl)octadec-8-enoate) (181 mg, 0.26 mmol) was reacted with pyridine (0.25 µl, 0.28 mmol) and stearyl chloride (95.6 mg, 0.31 mmol). Workup and preparative thin-layer chromatography gave the desired product as a colorless oil.

Yield: 20 mg, 3%.

$^1$H NMR (500 MHz, CDCl$_3$): δ [ppm]=5.43 (m, 2H, CH=CH), 5.15 (m, 2H, CH=CH), 4.04 (m, 4H, COOCH$_2$), 3.94 (t, 4H, COOCH$_2$—(CH$_2$)$_4$—CH$_2$OOC), 2.28 (m, 4H, CH$_2$COO), 1.98 (m, 4H, CH$_2$CH$_2$), 1.61 (m, 10H, CH$_2$CH$_2$COO+OCH$_2$CH), 1.45-1.11 (m, 108H), 0.88 (t, 12H, CH$_3$).

HRMS (ESI): calculated for $C_{80}H_{150}O_8Na^+$: 1261,1223; found: 1262,1246.

Example 19

Preparation of a mixture of (E)-9-((stearoyloxy)methyl)octadec-10-enoic acid and (E)-10-((stearoyloxy)methyl)octadec-8-enoic acid

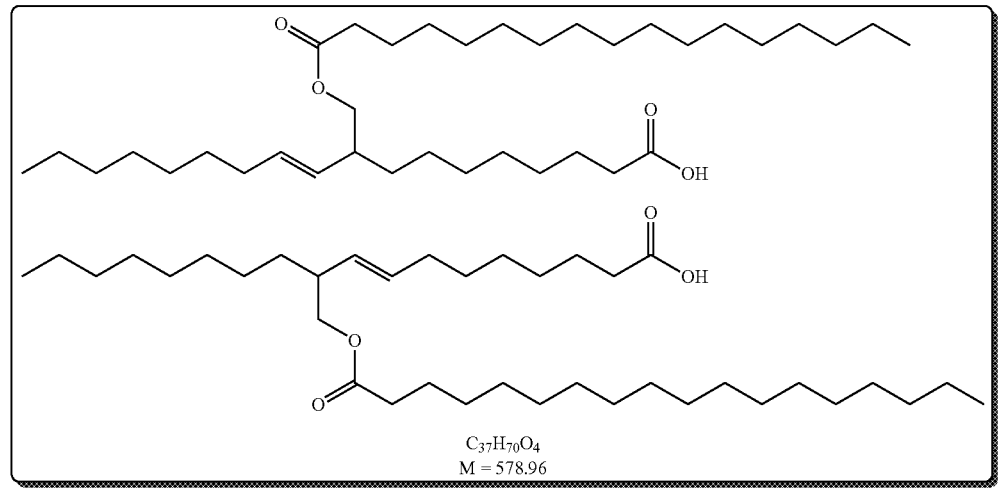

$C_{37}H_{70}O_4$
M = 578.96

The synthesis was according to GEM 5. A mixture of E-9-(hydroxymethyl)octadec-10-enoic acid and E-10-(hydroxymethyl)octadec-8-enoic acid (428 g, 1.3 mmol) was reacted with pyridine (0.13 ml, 1.65 mmol) and stearyl chloride (from stearic acid: 467 mg, 1.64 mmol). Workup and filtration through silica gel (cyclohexane:ethyl acetate 15:1 v/v) gave the desired product as a colorless wax.

Yield: 716 mg, 92%.

$^1$H NMR (500 MHz, CDCl$_3$): δ [ppm]=5.42 (m, 1H, CH=CH—CH), 5.21 (m, 1H, CH=CH—CH), 3.94 (m, 2H, CH—CH$_2$—O), 2.34 (m, 2H, CH$_2$COOH), 2.28 (m, 2H, CH$_2$—COOCH$_2$), 2.04-1.93 (m, 2H, CH$_2$—CH=CH), 1.61 (m, 5H. CH=CH—CH. CH$_2$—CH$_2$—COO), 1.25 (s, 47H), 0.88 (t, $^3$J=6.9 Hz, 6H, CH$_3$).

$^{13}$C NMR (125 MHz, CDCl$_3$): δ [ppm]=179.15, 179.07, 134.33, 133.88, 131.64, 131.30, 66.15, 66.10, 46.06, 34.01, 34.01, 32.82, 32.68, 32.03, 32.01, 31.27, 31.21, 29.82, 29.69, 29.68, 29.57, 29.45, 29.37, 29.29, 29.28, 29.26, 29.16, 28.99, 28.79, 27.24, 27.15, 27.07, 24.80, 24.75, 22.82, 22.81, 14.25.

HRMS (ESI): calculated for $C_{37}H_{70}O_4Na^+$: 601.5166; found: 601.5158.

EA: calculated for $C_{37}H_{70}O_4$ C: 76.76%, H: 12.19%, found: C: 76.71%, H: 12.42%.

Example 20

Preparation of a mixture of 2'-ethylhexyl (E)-9-((((E)-9-((stearoyloxy)methyl)octadec-10-enoyl)oxy)methyl)octadec-10-enoate 2'-ethylhexyl (E)-9-((((E)-9-((stearoyloxy)methyl)octadec-10-enoyl)oxy)methyl)octadec-8-enoate, 2'-ethylhexyl (E)-10-((((E)-9-((stearoyloxy)methyl)octadec-10-enoyl)oxy)methyl)octadec-10-enoate and 2'-ethylhexyl (E)-10-((((E)-9-((stearoyloxy)methyl)octadec-10-enoyl)oxy)methyl)octadec-8-enoate

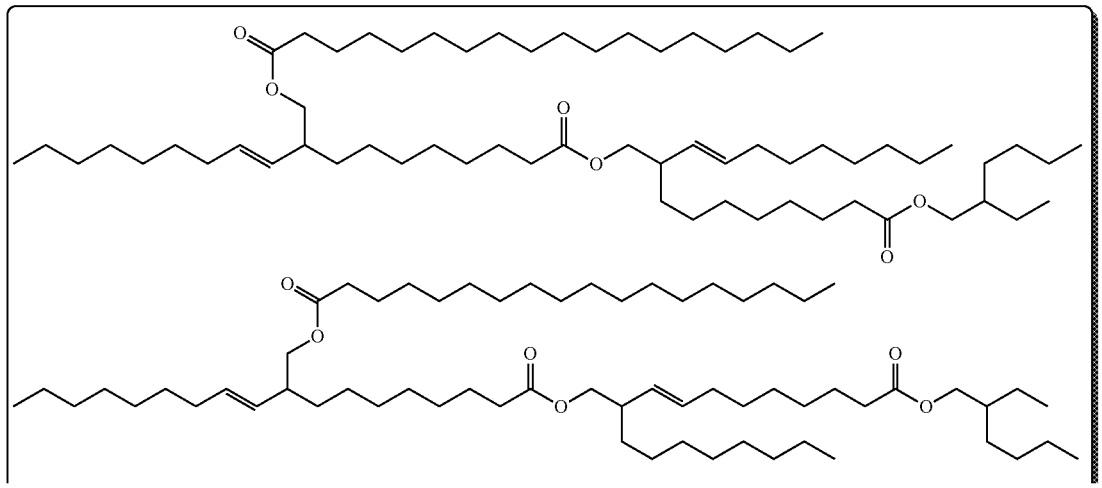

-continued

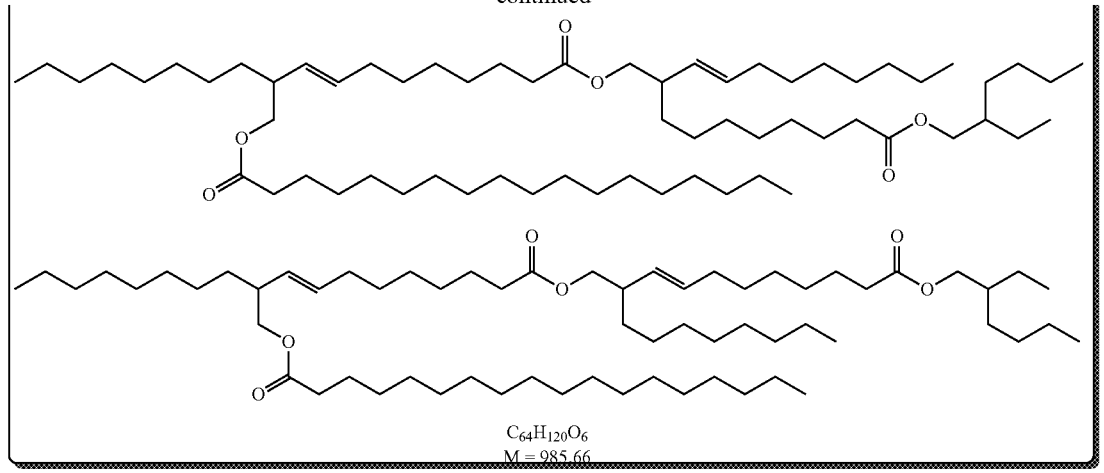

$C_{64}H_{120}O_6$
M = 985.66

A mixture of (E)-9-((stearoyloxy)methyl)octadec-10-enoic acid and (E)-10-((stearoyloxy)methyl)octadec-8-enoic acid (271 mg, 0.47 mmol) was initially charged together with a mixture of 2'-ethylhexyl E-9-(hydroxymethyl)octadec-10-enoate and 2'-ethylhexyl E-10-(hydroxymethyl)octadec-8-enoate (188 mg, 0.44 mmol) in toluene, and admixed with p-toluenesulfonic acid (84 mg, 0.44 mmol) and 4 Å molecular sieve (62 mg, 121.2 mg/mmol). After stirring at 40° C. for 2 h, ice was added. After phase separation, the aqueous phase was extracted three times with ethyl acetate (1:1 v/v). The combined organic phases were washed with saturated aqueous sodium hydrogencarbonate solution and then with saturated aqueous sodium chloride solution, dried over magnesium sulfate and concentrated to dryness under reduced pressure.

Column chromatography (cyclohexane: ethyl acetate 20:1 v/v) gave the desired product as a colorless oil.

Yield: 14 mg, 3%.

$^1$H NMR (500 MHz, CDCl$_3$): δ [ppm]=5.42 (m, 2H, CH=CH—CH), 5.21 (m, 2H, CH=CH—CH), 3.98 (m, 2H, CH—CH$_2$—O-ethylhexyl), 3.96-3.87 (m, 4H, CH—CH$_2$—O), 2.28(m, 6H, CH$_2$—COOCH$_2$), 1.98 (m, 4H, CH$_2$—CH=CH), 1.68-1.50 (m, 8H. CH=CH—CH. CH$_2$—CH$_2$—COO), 1.43-1.15 (s, 77H), 0.88 (t, $^3$J=4.7 Hz, 15H, CH$_3$).

$^{13}$C NMR (125 MHz, CDCl$_3$): δ [ppm]=174.21, 174.17, 174.05, 174.00, 173.96, 132.77, 132.47, 130.76, 130.75, 130.59, 67.74, 67.72, 66.79, 42.25, 42.20, 38.90, 34.59, 34.58, 34.55, 32.77, 32.72, 32.70, 32.08, 32.04, 31.61, 30.58, 29.86, 29.83, 29.82, 29.80, 29.69, 29.66, 29.52, 29.47, 29.46, 29.42, 29.40, 29.35, 29.34, 29.22, 29.21, 29.19, 29.17, 29.08, 28.95, 28.91, 27.05, 27.03, 25.20, 25.19, 25.16, 25.14, 23.95, 23.14, 22.85, 22.83, 14.27, 14.21, 11.15.

HRMS (ESI): calculated for C$_{64}$H$_{120}$O$_6$Na$^+$: 1007.8984; found: 1007.8977.

EA: calculated for C$_{37}$H$_{70}$O$_4$ C: 77.99%, H: 12.27%, found: C: 78.17%, H: 12.30%.

The invention claimed is:

1. A mixture of at least two ester compounds of the general formula (I)

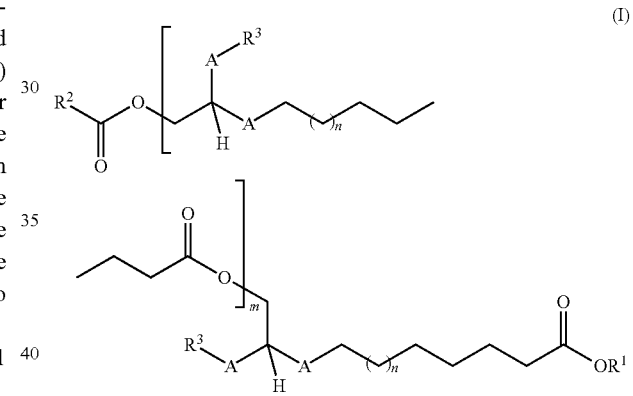

in which
the A radical is selected from the group consisting of CH$_2$, CH$_2$CH$_2$, cis-CH=CH and/or trans-CH=CH,
n is 0 or 1 to 20,
m is 1 to 20,
the R$^1$ radical is selected from the group consisting of hydrogen, branched or unbranched C$_1$- to C$_{60}$-alkyl radicals, branched or unbranched C$_2$- to C$_{60}$-alkenyl radicals, C$_7$- to C$_{60}$-arylalkyl radicals, C$_1$- to C$_{60}$-heteroarylalkyl radicals, C$_6$- to C$_{60}$-aryl radicals, and/or cyclically saturated or unsaturated C$_5$to C$_{60}$-alkyl radicals, where these are unsubstituted or mono- or polysubstituted by at least one substituent selected from the group of OH, R$^4$, R$^5$, O-acetyl,
the R$^2$ radical is selected from the group consisting of H, branched or unbranched C$_2$- to C$_{60}$-alkyl radicals, C$_2$- to C$_{60}$-heteroalkyl radicals, C$_7$- to C$_{60}$-arylalkyl radicals, C$_6$-to C$_{60}$-heteroarylalkyl radicals, C$_6$- to C$_{60}$-aryl radicals, and/or cyclically saturated or unsaturated C$_5$-to C$_{60}$-alkyl radicals, where these are unsubstituted or mono- or polysubstituted by at least one substituent selected from the group of OH, O—C(O)—R$^1$, CH$_2$OH, CO$_2$H, CO$_2$R$^1$, R$^5$, and also branched or unbranched C$_2$- to C$_{60}$-alkenyl radicals or methyl, where this is unsubstituted or mono- or polysubstituted by at least one substituent selected from the group of OH, O—C(O)—R$^1$, CH$_2$OH, CO$_2$H, CO$_2$R$^1$, R$^5$, the R$^3$ radical is selected from the group consisting of branched or unbranched C$_1$- to C$_{60}$-alkyl radicals, branched or unbranched C$_2$- to C$_{60}$-alkenyl radicals, C$_7$- to C$_{60}$-arylalkyl radicals and/or C$_6$- to C$_{60}$-heteroarylalkyl radicals, where these are unsubstituted or mono- or polysubstituted by at least one substituent selected from the group of OH, CH$_2$OH, CH$_2$—R$^4$, the R$^4$ radical has the following structure (II):

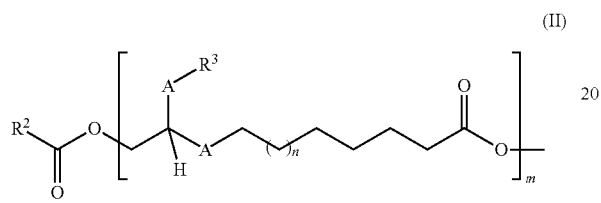

(II)

in which the R$^2$, R$^3$ and A radicals and the numbers m and n present therein are defined as described above, the R$^5$ radical has the following structure (III):

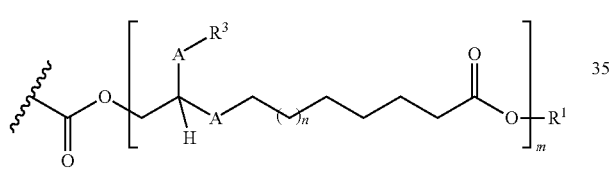

(III)

in which the R$^1$, R$^3$ and A radicals and the numbers m and n present therein are defined as described above.

2. The mixture of at least two ester compounds as claimed in claim 1, wherein each of the ester compounds in the mixture of at least two ester compounds of the general formula (I) has the general structure (Ia)

in which n' and n" are either 1 and 2 or 2 and 1, m' is 1 to 5, the R$^1$ radical is selected from the group consisting of hydrogen, branched or unbranched C$_1$- to C$_{60}$-alkyl radicals, branched or unbranched C$_2$- to C$_{60}$-alkenyl radicals, C$_7$- to C$_{60}$-arylalkyl radicals, C$_1$-to C$_{60}$-heteroarylalkyl radicals and/or C$_6$- to C$_{60}$-aryl radicals, the R$^2$ radical is selected from the group consisting of branched or unbranched C$_1$- to C$_{60}$-alkyl radicals, branched or unbranched C$_2$- to C$_{60}$-alkenyl radicals, C$_7$- to C$_{60}$-arylalkyl radicals and/or C$_6$- to C$_{60}$-heteroarylalkyl radicals and/or cyclically saturated and or unsaturated C$_5$- to C$_{60}$-alkyl radicals, where these are unsubstituted or mono- or polysubstituted by at least one substituent selected from the group of OH, CH$_2$OH.

3. The mixture of at least two ester compounds as claimed in claim 1, wherein each of the ester compounds in the mixture of at least two ester compounds of the general formula (I) has the general structure (Ib)

(Ia)

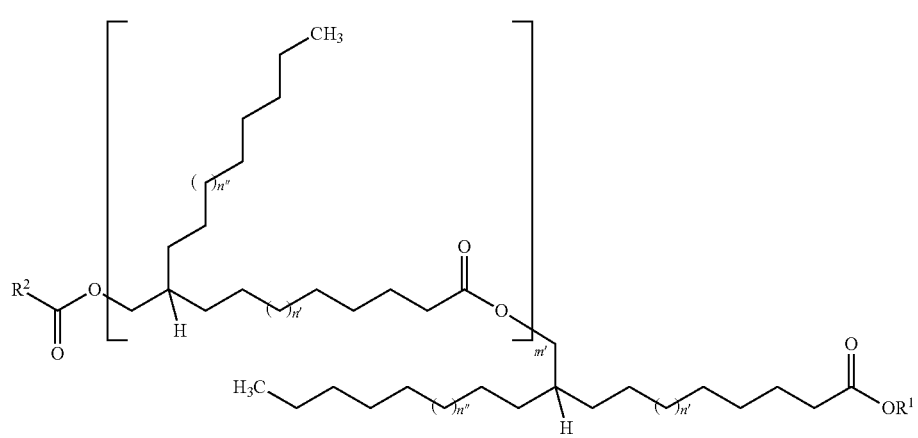

(Ib)

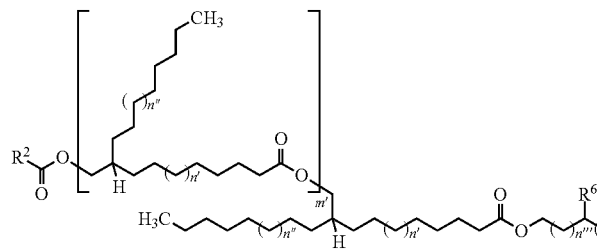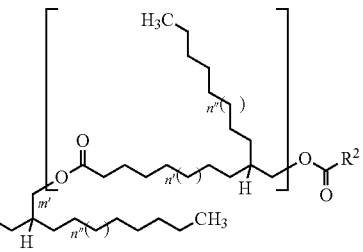

in which
n' and n" are either 1 and 2 or 2 and 1, n'" is 0 to 10, m' is 1 to 5, the $R^2$ radical is selected from the group consisting of branched or unbranched $C_1$- to $C_{60}$-alkyl radicals, branched or unbranched $C_1$- to $C_{60}$-alkenyl radicals, $C_7$- to $C_{60}$-arylalkyl radicals and/or $C_6$- to $C_{60}$-heteroarylalkyl radicals and/or cyclically saturated and or unsaturated $C_5$- to $C_{60}$-alkyl radicals, where these are unsubstituted or mono- or polysubstituted by at least one substituent selected from the group of OH, $CH_2OH$, $R^6$ radical is selected from the group consisting of branched or unbranched $C_1$- to $C_{60}$-alkyl radicals and branched or unbranched $C_2$- to $C_{60}$-alkenyl radicals.

4. The mixture of at least two ester compounds as claimed in claim 1, wherein each of the ester compounds in the mixture of at least two ester compounds of the general formula (I) has the general structure (Ic)

the $R^6$ radical is selected from the group consisting of branched or unbranched $C_1$- to $C_{60}$-alkyl radicals and branched or unbranched $C_2$- to $C_{60}$-alkenyl radicals.

5. The mixture of at least two ester compounds as claimed in claim 1, wherein two of the at least two ester compounds in each case are regioisomers of one another.

6. The mixture of least two ester compounds as claimed in claim 2, wherein two of the at least two ester compounds in each case are regioisomers of one another.

7. The mixture of least two ester compounds as claimed in claim 3, wherein two of the at least two ester compounds in each case are regioisomers of one another.

8. The mixture of least two ester compounds as claimed in claim 4, wherein two of the at least two ester compounds in each case are regioisomers of one another.

9. The mixture of least two ester compounds as claimed in claim 1, further comprising at least one further ester not having the general formula (I).

10. The mixture of least two ester compounds as claimed in claim 9, wherein the at least one further ester is selected from the group consisting of trimethylolpropane and pentaerythritol esters, TMP complex esters in fully or partly (Ic)

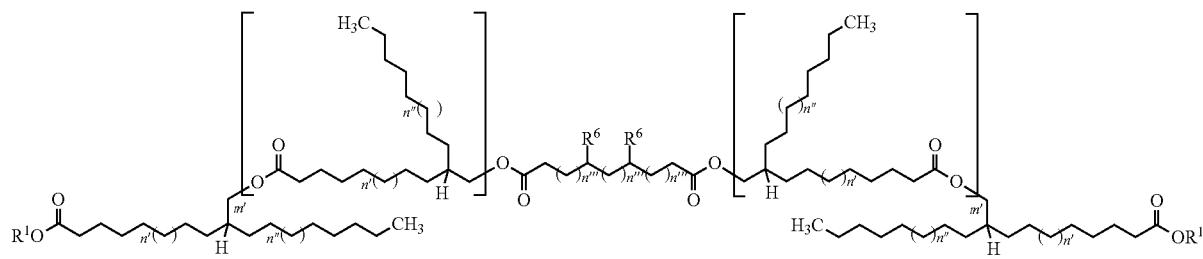

in which
n' and n" are either 1 and 2 or 2 and 1, n'" is 0 to 10, m' is 1 to 5,
the $R^1$ radical is selected from the group consisting of hydrogen, branched or unbranched $C_1$ to $C_{60}$-alkyl radicals, branched or unbranched $C_1$ to $C_{60}$-alkenyl radicals, $C_7$- to $C_{60}$-arylalkyl radicals, $C_1$- to $C_{60}$-heteroarylalkyl radicals and/or $C_6$- to $C_{60}$-aryl radicals, esterified form with saturated and/or mono- or polyunsaturated carboxylic acids of chain length C6-C36, where these may be linear or branched, complex esters of dimer acids, dimer acid esters, ethylhexyl dimerate, aliphatic carboxylic, dicarboxylic esters, phosphate esters, trimellitic and pyromellitic esters, and natural glyceride ester.

* * * * *